(12) United States Patent
Shkand et al.

(10) Patent No.: US 9,841,428 B2
(45) Date of Patent: Dec. 12, 2017

(54) VISCOSITY-SENSITIVE DYES AND METHOD

(71) Applicant: SETA BioMedicals, LLC, Urbana, IL (US)

(72) Inventors: Tetiana Vitaliivna Shkand, Kharkiv (UA); Mykola Oleksiiovych Chyzh, Kharkiv (UA); Iryna Vadymivna Sleta, Kharkiv (UA); Anatoliy Leonidovich Tatarets, Kharkiv (UA); Oleksandr Davydovych Roshal, Kharkiv (UA); Leonid Davidovych Patsenker, Kharkiv (UA); Borys Petrovych Sandomyrskiy, Kharkiv (UA); Ewald Alois Terpetschnig, Urbana, IL (US)

(73) Assignee: SETA BioMedicals, LLC, Urbana, IL (US)

(*) Notice: Subject to any disclaimer, the term of this patent is extended or adjusted under 35 U.S.C. 154(b) by 0 days.

(21) Appl. No.: 14/866,067

(22) Filed: Sep. 25, 2015

(65) Prior Publication Data

US 2016/0091495 A1    Mar. 31, 2016

(30) Foreign Application Priority Data

Sep. 26, 2014 (UA) .............................. A201410540

(51) Int. Cl.
| | |
|---|---|
| G01N 21/76 | (2006.01) |
| G01N 33/52 | (2006.01) |
| G01N 33/58 | (2006.01) |
| G01N 21/64 | (2006.01) |

(52) U.S. Cl.
CPC .......... *G01N 33/582* (2013.01); *G01N 33/52* (2013.01); *G01N 21/6408* (2013.01); *G01N 21/6456* (2013.01); *G01N 2021/6439* (2013.01)

(58) Field of Classification Search
CPC ....... G01N 21/76; G01N 33/582; G01N 33/52
USPC ........ 436/172, 94, 164; 422/50, 68.1, 82.05, 422/82.06, 82.07, 82.08, 82.09
See application file for complete search history.

(56) References Cited

U.S. PATENT DOCUMENTS

| | | | |
|---|---|---|---|
| 6,083,485 A * | 7/2000 | Licha | A61K 49/0017 424/1.11 |
| 6,140,494 A * | 10/2000 | Hamilton | C09B 57/007 536/26.6 |
| 6,403,807 B1 * | 6/2002 | Singh | C07D 487/14 436/546 |
| 6,538,129 B1 | 3/2003 | Terpetschnig et al. | |
| 7,250,517 B2 | 7/2007 | Terpetschnig et al. | |
| 2002/0077487 A1 | 6/2002 | Leung et al. | |

(Continued)

FOREIGN PATENT DOCUMENTS

WO    WO 2003/087052 A3    10/2003

*Primary Examiner* — Brian J Sines
(74) *Attorney, Agent, or Firm* — DASCENZO Intellectual Property Law, P.C.

(57) ABSTRACT

Disclosed viscosity-sensitive reporter compounds and methods allow tracing the changes in viscosity in a biological sample/environment (e.g., in medical, biochemical, biological, and/or pharmaceutical applications). Compounds and methods of the present disclosure can be used to identify the localization and the rheological state of hydrogels, their degradation products and other biostructural materials, including surgical implants, as well as the effectiveness of drug delivery by hydrogel carriers.

14 Claims, 15 Drawing Sheets

(56) References Cited

U.S. PATENT DOCUMENTS

| | | | |
|---|---|---|---|
| 2004/0171827 A1* | 9/2004 | Peng | C09B 47/32 |
| | | | 540/145 |
| 2006/0004188 A1* | 1/2006 | Leung | A61K 41/0057 |
| | | | 530/391.1 |
| 2012/0052481 A1* | 3/2012 | Rabbani | G01N 33/6803 |
| | | | 435/4 |

* cited by examiner

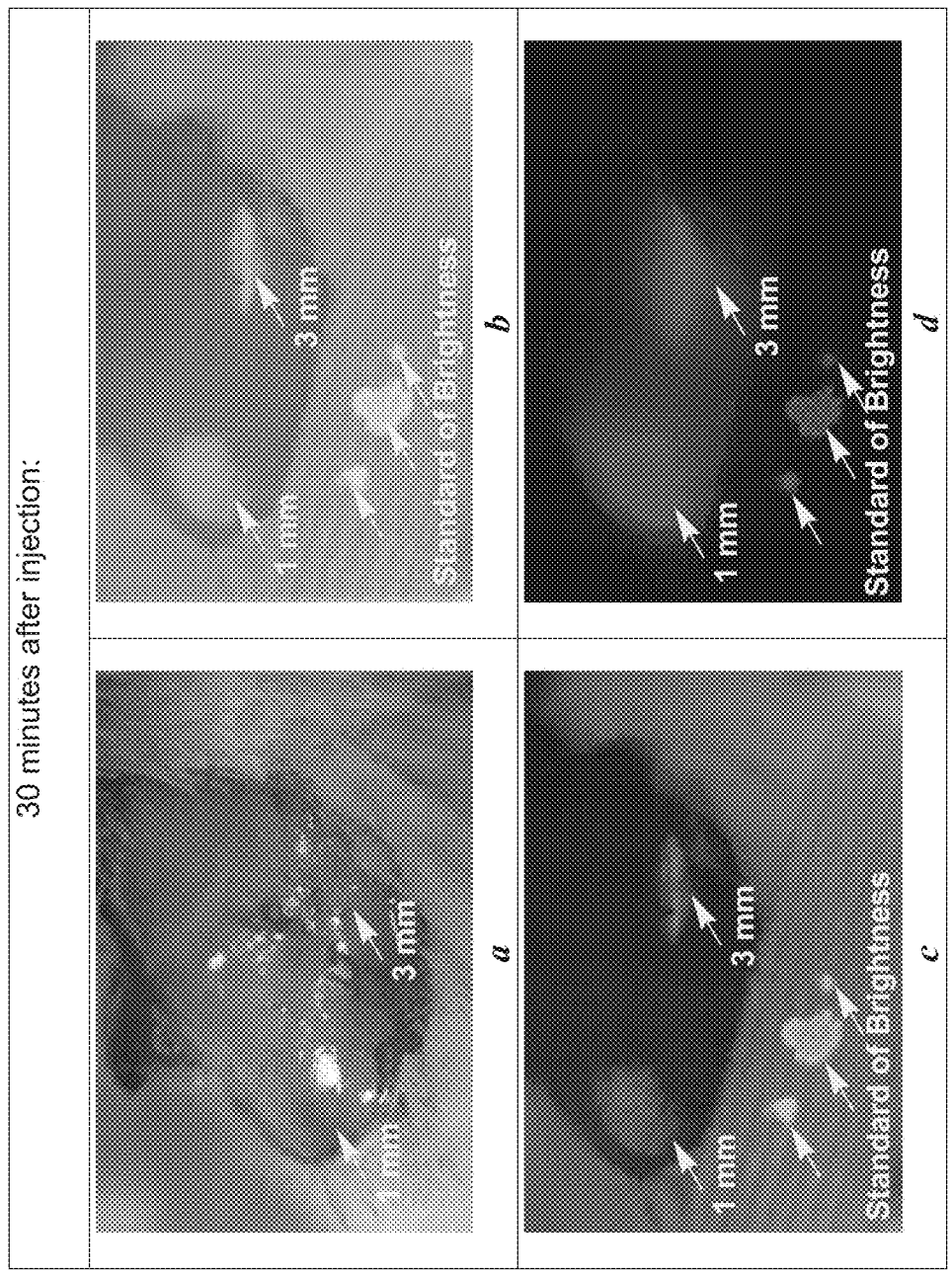
Fig. 8 (a-d)

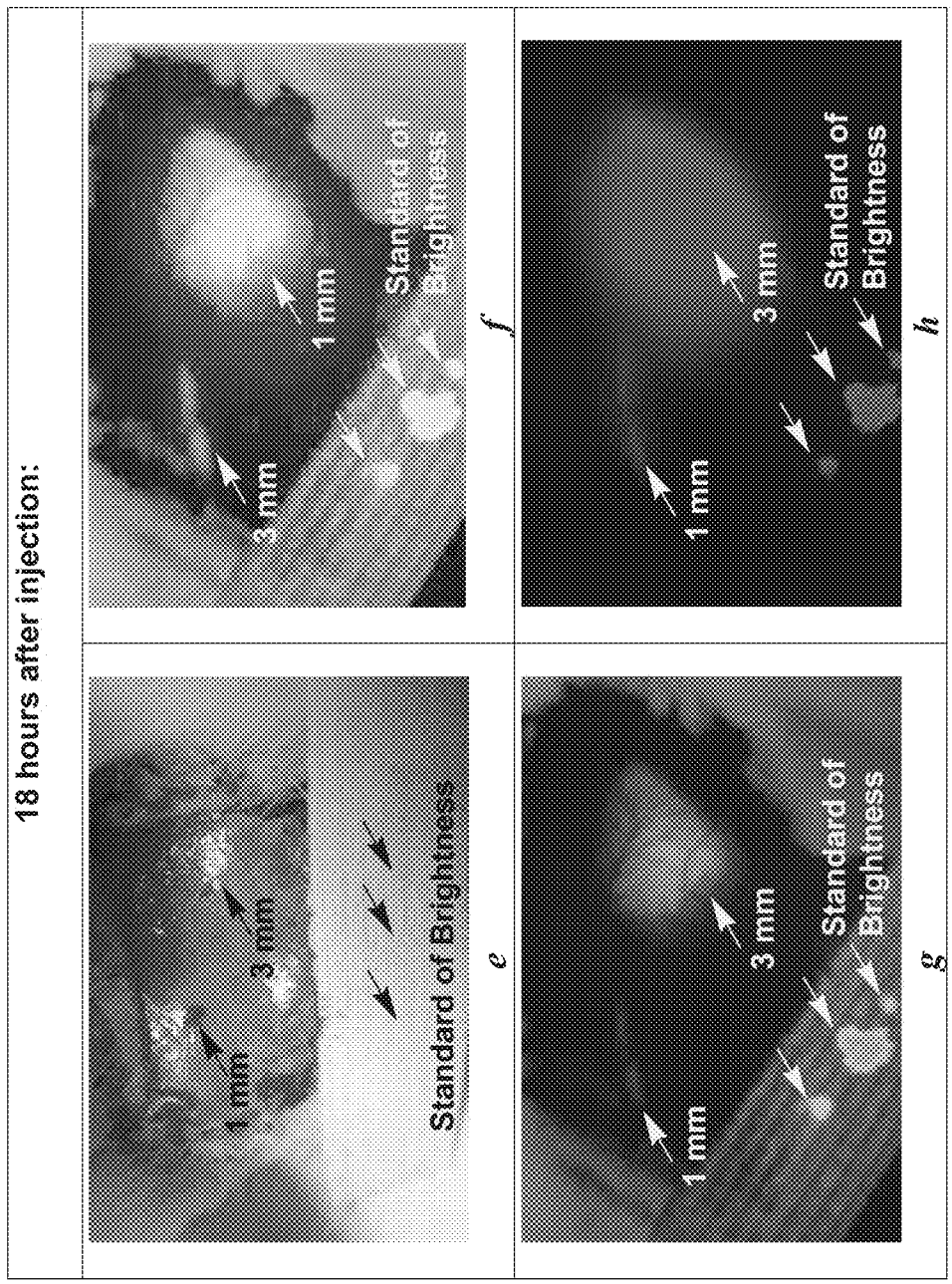
Fig. 8 (e-h)

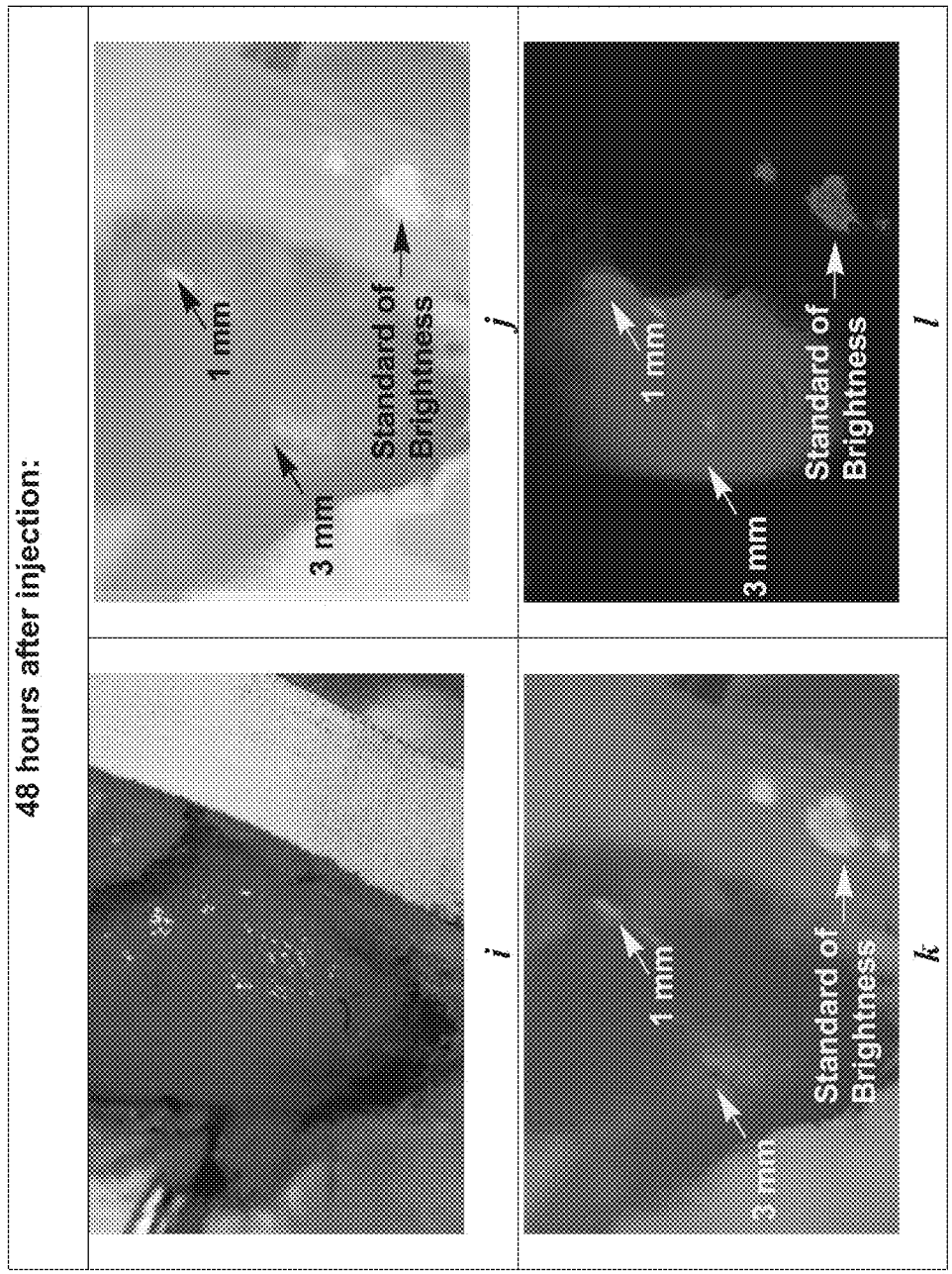
Fig. 8 (i—l)

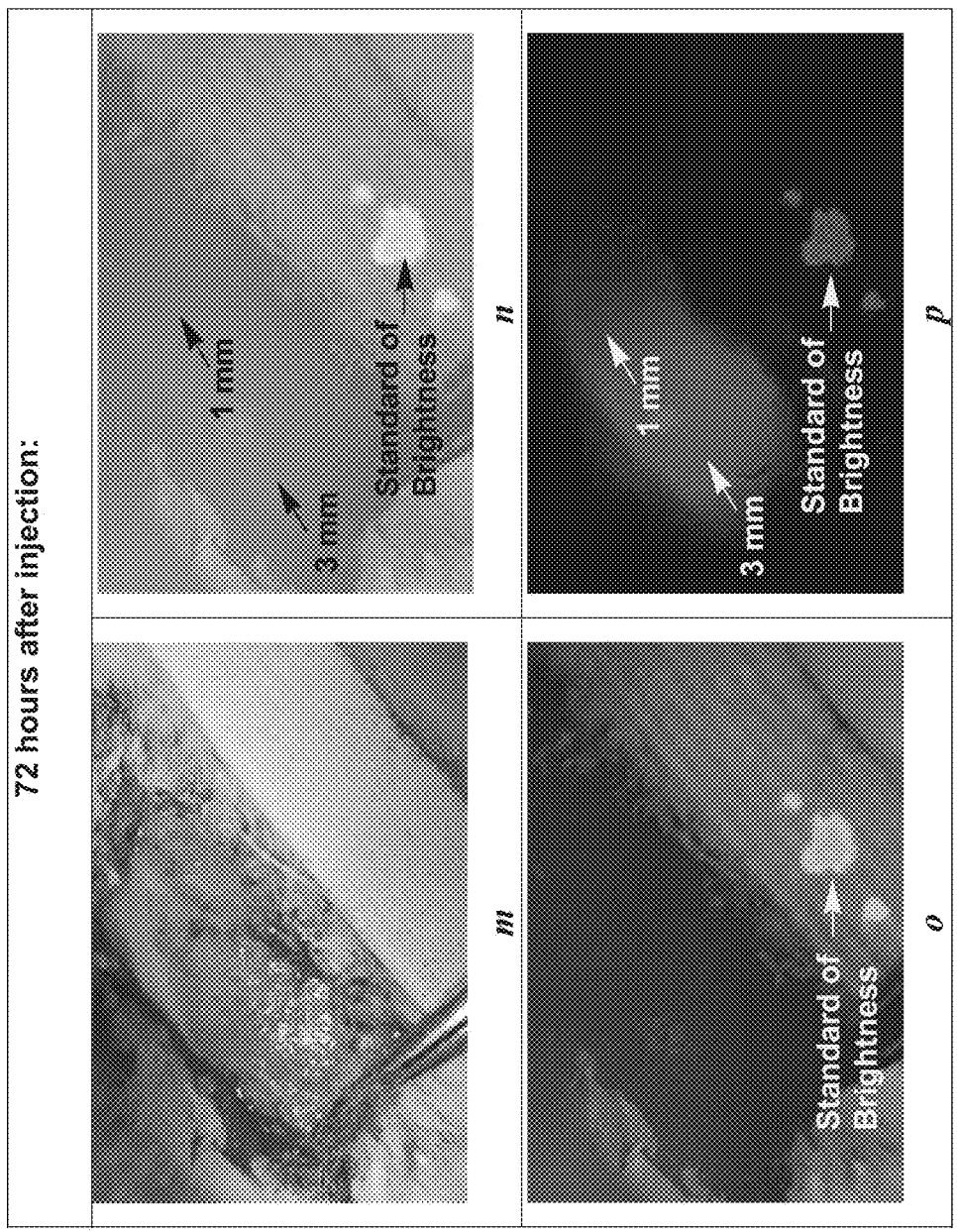
Fig. 8 (m—p)

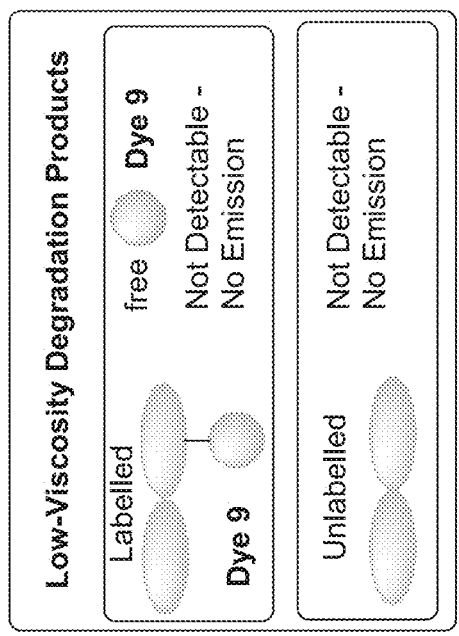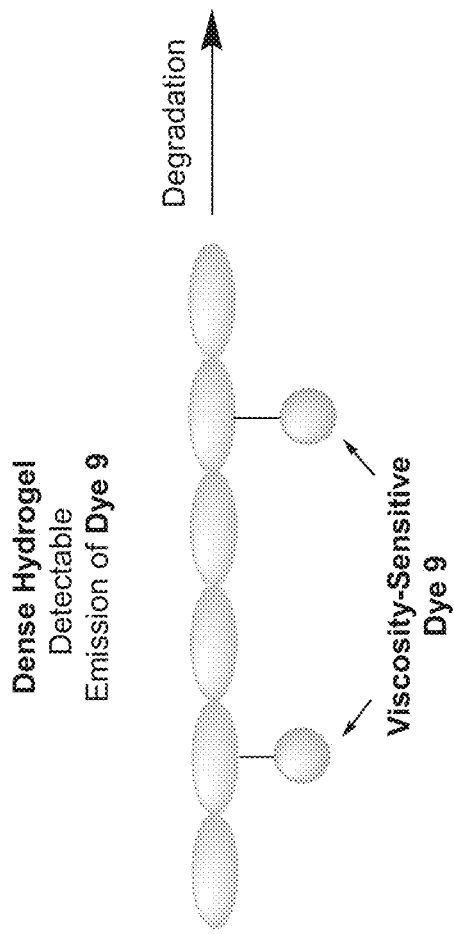
Fig. 12

VISCOSITY-SENSITIVE DYES AND METHOD

CROSS-REFERENCES TO RELATED MATERIALS

This application claims priority to Ukrainian Patent Application No. A201410540, filed Sep. 26, 2014, published Apr. 10, 2015 in Ukrainian Patent Bulletin No. 7, and entitled "СПОСІБ ВИЗНАЧЕННЯ ГІДРОГЕЛЮ В БІОЛОГІЧНИХ ТКАНИНАХ" (translated title: "Method of Determining of Hydrogel in Biological Tissues"), the complete disclosure of which is hereby incorporated by reference for all purposes. Additionally, all patents, patent applications (published, pending, or abandoned), and other patent and non-patent references cited anywhere in this application are hereby incorporated by reference in their entirety for all purposes.

FIELD

The present disclosure relates to viscosity-sensitive reporter compounds and methods.

BACKGROUND

Colorimetric and/or luminescent compounds may offer researchers the opportunity to use color and light to analyze samples, investigate reactions, and perform assays, either qualitatively or quantitatively. Generally, brighter, more photostable reporters may permit faster, more sensitive, and more selective methods to be utilized in such research.

While a colorimetric compound absorbs light, and may be detected by that absorbance, a luminescent compound, or luminophore, is a compound that emits light. A luminescence method, in turn, is a method that involves detecting light emitted by a luminophore, and using properties of that light to understand properties of the luminophore and its environment. Luminescence methods may be based on chemiluminescence and/or photoluminescence and/or sonoluminescence, among others, and may be used in spectroscopy, microscopy, immunoassays, and hybridization assays, among others.

Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including extinction coefficient, excitation and emission spectrum, Stokes' shift, luminescence lifetime, and quantum yield. An extinction coefficient is a wavelength-dependent measure of the absorbing power of a luminophore. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. The luminescence lifetime is the average time that a luminophore spends in the excited state prior to returning to the ground state and emission of a photon. The quantum yield is the ratio of the number of photons emitted to the number of photons absorbed by a luminophore.

Hydrogels are used in medicine as surgical implants (see e.g., Regenerative Medicine Applications in Organ Transplantation, G. Orlando, J. P. Lerut, S. Soker, R. J. Stratta (Ed.), Elsevier, 2014), including prevention of heart aneurysms during the post-infarction period (N. Landa et al. Effect of injectable alginate implant on cardiac re-modeling and function after recent and old infarcts in rat. Circulation, 2008, 117 (11), 1388-1396), as fillers to eliminate defects in bones and as alginate dressings for plugging deep infected wounds. Hydrogels are also used in clinical pharmacology as transport systems for the targeted delivery of drugs (Polyethylene Glycols—Advances in Research and Application. Ed. Q. A. Acton. ScholarlyEditions, Atlanta, Ga., 2013) as well as in many other medical, veterinary, biological and pharmaceutical applications (Progress in Molecular and Environmental Bioengineering—from Analysis and Modeling to Technology Applications. A. Carpi (Ed.). Chapter 5. S. K. H. Gulrez et al., Hydrogels: Methods of Preparation, Characterisation and Applications. InTech, 2011, 660. ISBN 978-953-307-268-5, DOI: 10.5772/771).

In all these applications, an important task is the visualization and monitoring of hydrogels and/or their biodegradation products (decomposition in biological tissues), in particular in real time, as well as determining the rheological properties of hydrogels, i.e. their mechanical resistance and viscoelastic characteristics.

Luminescent methods are commonly used for the detection of hydrogels in biological tissues in vivo as these methods are more sensitive compared to non-fluorescent methods as they only require $10^{-6}$-$10^{-9}$M concentrations of a luminescent reporter.

A current luminescence-based, non-invasive method for in-vivo monitoring of biodegradable gelatin hydrogels is based on the luminescence of a meso-brominated pentamethine cyanine dyes (E. A. Owens et al. Highly Charged Cyanine Fluorophores for Trafficking Scaffold Degradation. Biomed. Mater., 2013(8), 014109 (9pp). doi:10.1088/1748-6041/8/1/014109). However, these dyes have no reactive groups by which they can be covalently attached to hydrogel molecules. They are kept in the gelatin only due to weak hydrophobic interactions. As a result, these dyes can easily migrate from the gelatin. Moreover, due to these dyes having similar spectral and luminescence properties (intensity) in gelatin as in the free form they do not allow tracing of the hydrogel. In addition, the free dyes have a tendency to accumulate in the liver, lymph nodes and salivary glands.

Another method involves the in-vivo determination of PEG-dextran hydrogels and collagen using the covalently attached fluorescent dyes Texas Red and Fluorescein (N. Artzi et al. In vivo and in vitro Tracking of Erosion in Biodegradable Materials Using Non-invasive Fluorescence Imaging. Nat. Mater., 2011(10), 704-709).

The same approach is used in the non-invasive determination of chitosan membranes covalently labeled with tetrametyl rhodamine isothiocyanate (TRITC) (C. Cunha-Reis et al. Fluorescent Labeling of Chitosan for Use in Non-invasive Monitoring of Degradation in Tissue Engineering. J. Tissue Eng. Regen. Med., 2013 (7), 39-50). Collagen, covalently labeled with the cyanine dye ZW800-1 (S. H. Kim et al. Near-infrared Fluorescence Imaging for Noninvasive Trafficking of Scaffold Degradation. Sci. Rep. 2013 (3), 1198) and alginate hydrogel covalently labeled with Fluorescein isothiocyanate (FITC) (J. Liu et al. Synthesis, Characterization, and Application of Composite Alginate Microspheres with Magnetic and Fluorescent Functionalities. J. App. Polymer Sci. 2009 (113), 4042-4051; H. Zhu et al. Combined Physical and Chemical Immobilization of Glucose Oxidase in Alginate Microspheres Improves Stability of Encapsulation and Activity. Bioconj. Chem. 2005 (16), 1451-1458 and rhodamine B isothiocyanate (RITC). A method for the determination of a biodegradable hydrogel implant based on PEGylated fibrinogen (PF), covalently bound to the fluorescent cyanine dye Cy5.5 NHS ester (Cy5.5-NHS) was previously disclosed [Regenerative medicine applications in organ transplantation. Ed. G. Orlando, J. P. Lerut, S. Soker, R. J. Stratta, Elsevier, 2014, 452-453]. Hydrogel implants in form of cylindrical plugs, spherical micro-beads, or hydrogel precursors (chemicals, from which the hydrogel is generated by thickening or polymerization) are injected and polymerized in-situ, i.e. directly at the site of introduction. Cy5.5 provides a fluorescent signal for in-vivo determination and quantification of the resorption of the hydrogel and its degradation products, which are covalently bound to Cy5.5 as well as free Cy5.5 eliminated from the hydrogel during its degradation.

Covalent attachment of the dye molecules prevents their separation from the hydrogel molecules, but the dyes used are not sensitive to the environment, i.e. their spectral characteristics, such as the luminescence wavelength and/or intensity do not change upon changing the properties of the medium (viscosity, polarity and hydrophilicity). These methods therefore cannot differentiate between the non-degraded, dense hydrogel (e.g. hydrogel implant or carrier) with high viscosity and the lower-density hydrogel degradation products with low viscosity, and are not capable to detect the dense hydrogel. Moreover, the luminescence contribution of free dye eliminated from the dense hydrogel during the degradation process further makes it impossible to differentiate between the dense and degraded hydrogel regions. Therefore, these methods are incapable to determine rheological properties of a hydrogel (FIG. 1).

Importantly, luminescence based methods that allow differentiation between and/or localization of the high density hydrogels and their degradation products, e.g., by characterizing the rheological state of the hydrogel, have NOT been disclosed previously.

SUMMARY

This disclosure relates to viscosity-sensitive reporter compounds and methods that allow tracing the changes in viscosity in a biological sample/environment (e.g., in medical, biochemical, biological, and/or pharmaceutical applications). Compounds and methods of the present disclosure can be used to identify the localization and the rheological state of hydrogels, their degradation products and other biostructural materials, including surgical implants, as well as the effectiveness of drug delivery by hydrogel carriers.

BRIEF DESCRIPTION OF THE DRAWINGS

FIG. 8 Hydrogel implant in rat hip. Monitoring of the different rheological states of an injected hydrogel implant using Dyes 9 (green channel) and Seta-650 dye (red channel). Images are shown in: normal light (a, e, i, m), combination of green and red channels (b, f, j, n), green channel (c, g, k, o), and red channel (d, h, l, p) at 30 minutes after injection (a-d), 18 hours after injection (e-h), 48 hours after injection (i-l), and 72 hours after injection (m-p).

FIG. 12 Viscosity-sensitive dyes are capable to detect only the dense labeled hydrogel. Labeled hydrogel degradation products as well as the free dye eliminated from the hydrogel during the degradation process are barely fluorescent.

DESCRIPTION

Abbreviations

Figure 1:
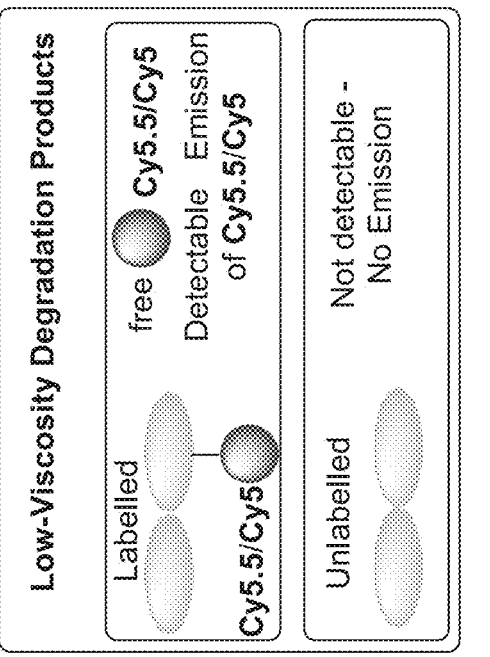
FIG. 1 Environment-insensitive dyes such as Cy5/Cy5.5 are capable to detect (1) the dense hydrogel labeled with dye; (2) hydrogel degradation products labeled with dye; and (3) free dye eliminated from the hydrogel.

The following abbreviations, among others, may be used in this application:

| Abbreviation | Definition |
| --- | --- |
| Bu | Butyl |
| DMF | N,N-dimethylformamide |
| DIPEA | N,N-diisopropylethylamine |
| Et | Ethyl |
| g | Grams |
| h | Hours |

| Abbreviation | Definition |
|---|---|
| L | Liters |
| m | milli ($10^{-3}$) |
| M | Molar |
| Me | Methyl |
| mol | Moles |
| nm | nanometer ($10^{-9}$ meter) |
| NHS | N-hydroxysuccinimide |
| μ | micro ($10^{-6}$) |
| PEG | polyethylene glycol |
| TSTU | N,N,N',N'-tetramethyl(succinimido)uronium tetrafluoroborate |

The dyes and methods of the present disclosure relate generally to novel luminescent dyes sensitive to viscosity and to methods of using these and other viscosity sensitive dyes.

The dyes and methods of the present disclosure may utilize the novel approach of using viscosity-sensitive fluorescent labels (reactive dyes) for monitoring the localization of the dense hydrogel as well as its degradation products. This approach is enabled using a fluorescent dye that is sensitive to the viscosity of the hydrogel, or by simultaneously using at least two fluorescent dyes, where at least one of the dyes is sensitive to the viscosity of the hydrogel, and the other is insensitive to environment viscosity, polarity and hydrophilicity. Moreover, if these dyes have different spectral characteristics, such as the different excitation and/or emission wavelengths and/or different luminescence lifetimes, the dyes and methods of the present disclosure allow for the simultaneous detection of the dense hydrogel together with the degraded hydrogels of low viscosity.

A number of viscosity sensitive dyes are reported in the literature as molecular rotors. Reactive versions of molecular rotors as reported in: M. K. Kuimova, Phys. Chem. Chem. Phys., 2012, 14, 12671-12686 or M. A. Haidekker et al. in A. P. Demchenko (ed.), Advanced Fluorescence Reporters in Chemistry and Biology I: Fundamentals and Molecular Design, Springer Ser Fluoresc (2010) 8: 267-308, would also be suitable for the detection of hydrogels.

In general, any reactive, viscosity-insensitive dye can be combined with the viscosity-sensitive labels, as long as the spectral properties and/or other luminescent properties allow differentiation between the dense hydrogel and the low density hydrogel decomposition products.

Viscosity-insensitive reactive dyes are available from many commercially available sources including: CF dyes (Biotium), BODIPY (Invitrogen), Alexa Fluor (Invitrogen), DyLight Fluor, (Thermo Scientific, Pierce), Atto Dyes (Atto-Tec and Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Cal Fluor dyes (Biosearch Technologies), Cy Dyes (GE), among others.

In one aspect, certain dyes that are sensitive to viscosity changes (viscosity-sensitive dyes) are based on the following structure:

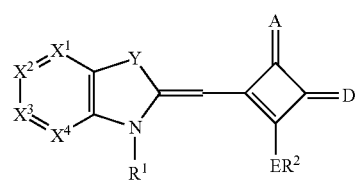

where A and D are selected from the group consisting of =O, =S, =Se, =Te, =N—$R^a$, and =C($R^b$)($R^c$);

E is selected from the group consisting of —O—, —S—, —Se—, —Te—, —(N—$R^a$)—, and —(C($R^b$)($R^c$))—;

$R^2$ is selected from the group consisting of H, alkyl, and a positive counter-ion;

Ra is selected from the group consisting of H, aliphatic, aromatic, alicyclic, aryl-alkyl, linked carriers, reactive substituents, reactive aliphatic substituents, —COOH, —CN, —OH, —$SO_3H$, —$SO_3R^m$, —$PO_3H_2$, —O—$PO_3H_2$, —$PO_3R_2^m$, —O—$PO_3R_2^m$, —$CONHR^m$, —$CONH_2$, COO—NHS and COO—$R^m$; each aliphatic residue may incorporate up to 20 heteroatoms selected from N, O, and S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

$R^b$ and $R^c$ are independently selected from the group consisting of H, aliphatic, aromatic, alicyclic, aryl-alkyl, -L-$S_c$, -L-$R^x$, -L-$R^\pm$, —COOH, —CN, —OH, —$SO_3H$, —$PO_3H_2$, —O—$PO_3H_2$, —$PO_3R_2^m$, —O—$PO_3R_2^m$, —$CONHR^m$, —$CONH_2$, —COO—NHS and —COO—$R^m$; each aliphatic residue may incorporate up to 20 heteroatoms selected from N, O, and S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; or adjacent $R^b$ and $R^c$, taken in combination, form a cyclic or heterocyclic ring structure that is optionally substituted by -L-$S_c$, -L-$R^x$ or -L-$R^\pm$;

$R^m$ is selected from the group consisting of aliphatic groups, —$(CH_2)_y$—$S_c$, —$(CH_2)_y$—$R^x$, —$(CH_2)_y$—$R^\pm$, —$(CH_2)_y$—O—$(CH_2)_y$—$S_c$, —$(CH_2)_y$—O—$(CH_2)_y$—$R^x$, —$(CH_2)_y$—O—$(CH_2)_y$—$R^\pm$, and aromatic substituents, where each y is independently 1 to 20;

L is a covalent linkage that is linear or branched, cyclic or heterocyclic, saturated or unsaturated, having 1-60 nonhydrogen atoms from the group consisting of C, N, P, O and S, in such a way that the linkage contains any combination of ether, thioether, amine, ester, amide bonds; single, double, triple or aromatic carbon-carbon bonds; carbon-sulfur bonds, carbon-nitrogen bonds, phosphorus-sulfur bonds, nitrogen-nitrogen bonds, nitrogen-oxygen bonds, nitrogen-platinum bonds, or aromatic or heteroaromatic bonds;

$R^x$ is a reactive group;

$S_c$ is a conjugated substance;

$R^\pm$ is an ionic group;

Y is independently selected from the group consisting of O, S, N—$R^d$, $CR^e$=$CR^f$ and C($R^i$)($R^j$), wherein $R^d$ is selected from the group consisting of H, aliphatic groups, alicyclic groups, aromatic groups, -L-$S_c$, -L-$R^x$, -L-$R^\pm$, and —$CH_2$—CONH—$SO_2$-Me;

$R^e$, $R^f$, $R^i$, and $R^j$ are independently selected from the group consisting of H, aliphatic groups, alicyclic groups, aromatic groups, -L-$S_c$, -L-$R^x$, —$R^x$, -L-$R^\pm$, —$R^x$, —$R^\pm$, —$CH_2$—CONH—$SO_2$-Me, —COOH, —CN, —OH, —$SO_3H$, —$PO_3H_2$, —O—$PO_3H_2$, —$PO_3R_2^m$, —O—$PO_3R_2^m$, —$CONHR^m$, —$CONH_2$, —COO—NHS and —COO—$R^m$; each aliphatic residue may incorporate up to 20 heteroatoms selected from N, O, and S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; or $R^i$ and $R^j$, taken in combination, form a ring-system that is optionally further substituted by one or more reactive or ionic substituents;

$R^1$ is selected from the group consisting of H, aliphatic groups, alicyclic groups, alkylaryl groups, aromatic groups, -L-$S_c$, -L-$R^x$, -L-$R^\pm$, and —$CH_2$—CONH—$SO_2$-Me; each aliphatic residue may incorporate up to 20 heteroatoms selected from N, O, S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

each of $X^1$, $X^2$, $X^3$, and $X^4$ are independently selected from the group consisting of N, $NR^K$, O, S, and C—$R^T$, where $R^K$ is hydrogen, alkyl, arylalkyl and aryl groups, -L-$S_c$, -L-$R^x$, -L-$R^\pm$, or —$CH_2$—CONH—$SO_2$-Me, where each aliphatic residue may incorporate up to 20 heteroatoms selected from N, O, S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; $R^T$ is hydrogen, -L-$S_c$, -L-$R^x$, -L-$R^\pm$, —$R^x$, —$R^\pm$, —$CH_2$—CONH—$SO_2$-Me, amino, alkylamino, dialkylamino, trialkylammonium, sulfo, trifluoromethyl, alkoxy, halogen, carboxy, hydroxy, phosphate, sulfate, an aliphatic group, an alicyclic group, or aromatic group; each aliphatic residue may incorporate up to 20 heteroatoms selected from N, O, S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; or adjacent $R^K$ substituents, $R^T$ substituents, or $R^K$ and $R^T$ substituents, taken in combination, form a fused aromatic or heterocyclic ring that is optionally substituted by H, alkyl, aryl, cycloalkyl L-$S_c$, L-$R^x$, L-$R^\pm$, —$R^x$ or —$R^\pm$; and each H may be independently substituted by a fluorine.

In another aspect, the methods of the present disclosure may relate to analytical methods that include viscosity-sensitive dyes and viscosity-insensitive dyes (e.g., environment-insensitive dyes).

Overview of Structures

Reactive Groups $R^x$

The fluorescent dye component of the present disclosure may include one or more reactive groups, where a reactive group generally is a group capable of covalent attachment with another molecule or substrate. Such other molecules or substrates may include hydrogels, proteins, carbohydrates, nucleic acids, and plastics, among others. Reactive groups vary in their specificity, and may preferentially react with particular functionalities and molecule types. Thus, reactive compounds generally include reactive groups selected to react preferentially with functionalities found on the molecule or substrate with which the reactive compound is intended to react.

The compounds of the present disclosure are optionally substituted, either directly or via a substituent, by one or more chemically reactive functional groups that may be useful for covalently attaching the compound to a desired substance. Each reactive group, or $R^x$, may be bound to the compound directly by a single covalent bond, or may be attached via a covalent spacer or linkage, L, and may be depicted as -L-$R^x$.

The reactive functional group $R^x$ may be selected from the following functionalities, among others: activated carboxylic esters, acyl azides, acyl halides, acyl nitriles, aldehydes, ketones, alkyl halides, alkyl sulfonates, anhydrides, aryl halides, aziridines, boronates, carboxylic acids, carbodiimides, diazoalkanes, epoxides, haloacetamides, halotriazines, imido esters, isocyanates, isothiocyanates, maleimides, phosphoramidites, silyl halides, sulfonate esters, and sulfonyl halides.

In particular, the following reactive functional groups, among others, are particularly useful for the preparation of labeled molecules or substances, and are therefore suitable reactive functional groups for the purposes of the reporter compounds:

a) N-hydroxysuccinimide esters, isothiocyanates, and sulfonylchlorides, which form stable covalent bonds with amines, including amines in proteins and amine-modified nucleic acids;

b) Iodoacetamides and maleimides, which form covalent bonds with thiol-functions, as in proteins;

c) Carboxyl functions and various derivatives, including N-hydroxybenztriazole esters, thioesters, p-nitrophenyl esters, alkyl, alkenyl, alkynyl, and aromatic esters, and acyl imidazoles;

d) Alkylhalides, including iodoacetamides, bromoacetamides and chloroacetamides;

e) Hydroxyl groups, which can be converted into esters, ethers, and aldehydes;

f) Aldehydes and ketones and various derivatives, including hydrazones, oximes, and semicarbozones;

g) Isocyanates, which may react with amines;

h) Activated C=C double-bond-containing groups, which may react in a Diels-Alder reaction to form stable ring systems under mild conditions;

i) Thiol groups, which may form disulfide bonds and react with alkylhalides (such as iodoacetamide);

j) Alkenes, which can undergo a Michael addition with thiols, e.g., maleimide reactions with thiols;

k) Phosphoramidites, which can be used for direct labeling of nucleosides, nucleotides, and oligonucleotides, including primers on solid or semi-solid supports;

l) Primary amines that may be coupled to a variety of groups including carboxyl, aldehydes, ketones, and acid chlorides, among others;

m) Boronic acid derivatives that may react with sugars;

n) Pyrylium moieties react with primary amines;

o) Haloplatinates form stable platinum complexes with amines, thiols and heterocycles;

p) Aryl halides react with thiols and amines.

R Groups

The R moieties associated with a dye may include any of a number of groups, as described above, including but not limited to alicyclic groups, aliphatic groups, aromatic groups, and heterocyclic rings, as well as substituted versions thereof.

Aliphatic groups may include groups of organic compounds characterized by straight- or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked and may contain one or more heteroatoms (such as polyethers and polyamines, among others).

As used herein, "alicyclic groups" include hydrocarbon substituents that incorporate closed rings. Alicyclic substituents may include rings in boat conformations, chair conformations, or resemble bird cages. Most alicyclic groups are derived from petroleum or coal tar, and many can be synthesized by various methods. Alicyclic groups may optionally include heteroalicyclic groups that include one or more heteroatoms, typically nitrogen, oxygen, or sulfur. These compounds have properties resembling those of aliphatics and should not be confused with aromatic compounds having the hexagonal benzene ring. Alicyclics may comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aromatic groups may include groups of unsaturated cyclic hydrocarbons containing one or more rings. A typical aromatic group is benzene, which has a 6-carbon ring formally containing three double bonds in a delocalized ring system. Aromatic groups may be highly reactive and chemically versatile. Most aromatics are derived from petroleum and coal tar. Heterocyclic rings include closed-ring structures, usually of either 5 or 6 members, in which one or more of the atoms in the ring is an element other than carbon, e.g., sulfur, nitrogen, etc. Examples include pyridine, pyrole, furan, thiophene, and purine. Some 5-membered heterocyclic compounds exhibit aromaticity, such as furans and thiophenes, among others, and are analogous to aromatic compounds in reactivity and properties.

Any substituent of the compounds of the present disclosure, including any aliphatic, alicyclic, or aromatic group, may be further substituted one or more times by any of a variety of substituents, including without limitation, F, Cl, Br, I, carboxylic acid, sulfonic acid, CN, nitro, hydroxy, phosphate, phosphonate, sulfate, cyano, azido, amine, alkyl, alkoxy, trialkylammonium or aryl. Aliphatic residues can incorporate up to six heteroatoms selected from N, O, S. Alkyl substituents include hydrocarbon chains having 1-22 carbons, more typically having 1-6 carbons, sometimes called "lower alkyl".

As described in WO 01/11370, sulfonamide groups such as —(CH$_2$), —SO$_2$—NH—SO$_2$—R, —(CH$_2$)$_n$—CONH—SO$_2$—R, —(CH$_2$)$_n$—SO$_2$—NH—CO—R, and —(CH$_2$)$_n$—SO$_2$NH—SO$_3$H, where R is aryl or alkyl and n=1-6, can be used to reduce the aggregation tendency and have positive effects on the photophysical properties of cyanines and related dyes. Where a substituent R is further substituted by a functional group that is formally electronically charged, such as for example a carboxylic acid, sulfonic acid, phosphoric acid, phosphonate or a quaternary ammonium group, the resulting ionic substituent R$^\pm$ may serve to increase the overall hydrophilicity of the compound. Examples of electronically charged functional groups include —PO$_3^{2\ominus}$, —O—PO$_3^{2\ominus}$, —PO$_3$R$^{m\ominus}$, —O—PO$_3$R$^{m\ominus}$, —C$_6$H$_4$—SO$_3^\ominus$, —C$_6$H$_4$—PO$_3^\ominus$, pyridylium, pyrylium, —SO$_3^\ominus$, —O—SO$_3^\ominus$, —COO$^\ominus$ and ammonium, among others.

As used herein, functional groups such as "carboxylic acid," "sulfonic acid," and "phosphoric acid" include the free acid moiety as well as the corresponding metal salts of the acid moiety, and any of a variety of esters or amides of the acid moiety, including without limitation alkyl esters, aryl esters, and esters that are cleavable by intracellular esterase enzymes, such as alpha-acyloxyalkyl ester (for example acetoxymethylene esters, among others). Further these esters might contain additional reactive or ionic groups and linked carriers.

The compounds of the present disclosure are optionally further substituted by a reactive functional group R$^x$, or a conjugated substance S$_c$, as described below.

The compounds of the present disclosure may be depicted in structural descriptions as possessing an overall charge. It is to be understood that the compounds depicted include an appropriate counter ion or counter ions to balance the formal charge present on the compound. Further, the exchange of counter ions is well known in the art and readily accomplished by a variety of methods, including ion-exchange chromatography and selective precipitation, among others.

Carriers and Conjugated Substances S$_c$

The reporter compounds of the present disclosure, including synthetic precursor compounds, may be covalently or non-covalently associated with one or more substances. Covalent association may occur through various mechanisms, including a reactive functional group as described above, and may involve a covalent linkage, L, separating the compound or precursor from the associated substance (which may therefore be referred to as -L-S$_c$).

The covalent linkage L binds the respective reactive group R$^x$, conjugated substance S$_c$ or ionic group R$^\pm$ to the dye molecule, either directly (L is a single bond) or with a combination of stable chemical bonds, that include single, double, triple or aromatic carbon-carbon bonds; carbon-sulfur bonds, carbon-nitrogen bonds, phosphorus-sulfur bonds, nitrogen-nitrogen bonds, nitrogen-oxygen or nitrogen-platinum bonds, or aromatic or heteroaromatic bonds; L may include ether, thioether, carboxamide, sulfonamide, urea, urethane or hydrazine moieties. In particular, L may include a combination of single carbon-carbon bonds and carboxamide or thioether bonds.

Where the substance is associated noncovalently, the association may occur through various mechanisms, including incorporation of the compound or precursor into or onto a solid or semisolid matrix, such as a bead or a surface, or by nonspecific interactions, such as hydrogen bonding, ionic bonding, or hydrophobic interactions (such as Van der Waals forces). The associated carrier may be selected from the group consisting of polypeptides, polynucleotides, polysaccharides, beads, microplate well surfaces, metal surfaces, semiconductor and non-conducting surfaces, nano-particles, and other solid surfaces.

The associated or conjugated substance may be associated with or conjugated to more than one reporter compound, which may be the same or different. Generally, methods for the preparation of dye-conjugates of biological substances are well-known in the art. See, for example, Haugland et al., MOLECULAR PROBES HANDBOOK OF FLUORESCENT PROBES AND RESEARCH CHEMICALS, Eighth Edition (1996), which is hereby incorporated by reference. Typically, the association or conjugation of a chromophore or luminophore to a substance imparts the spectral properties of the chromophore or luminophore to that substance.

Useful substances for preparing conjugates according to the present disclosure include, but are not limited to hydrogels, amino acids, peptides, proteins, nucleosides, nucleotides, nucleic acids, carbohydrates, lipids, ion-chelators, nonbiological polymers, cells, and cellular components. The substance to be conjugated may be protected on one or more functional groups in order to facilitate the conjugation, or to insure subsequent reactivity.

Where the substance is a peptide, the peptide may be a dipeptide or larger, and typically includes 5 to 36 amino acids. Where the conjugated substance is a protein, it may be an enzyme, an antibody, lectin, protein A, protein G, one or more hormones, or a phycobiliprotein. The conjugated substance may be a nucleic acid polymer, such as for example DNA oligonucleotides, RNA oligonucleotides (or hybrids thereof), or single-stranded, double-stranded, triple-stranded, or quadruple-stranded DNA, or single-stranded or double-stranded RNA.

Another class of conjugated substances includes carbohydrates that are polysaccharides, such as dextran, heparin, glycogen, starch and cellulose.

The associated or conjugated substance may be a member of a specific binding pair, and therefore useful as a probe for the complementary member of that specific binding pair, each specific binding pair member having an area on the surface or in a cavity which specifically binds to and is complementary with a particular spatial and polar organization of the other. The conjugate of a specific binding pair member may be useful for detecting and optionally quantifying the presence of the complementary specific binding pair member in a sample, by methods that are well known in the art.

Representative specific binding pairs may include ligands and receptors, and may include but are not limited to the following pairs: antigen-antibody, biotin-avidin, biotin-streptavidin, IgG-protein A, IgG-protein G, carbohydrate-lectin, enzyme-enzyme substrate; ion-ion-chelator, hormone-hormone receptor, protein-protein receptor, drug-drug receptor, DNA-antisense DNA, and RNA-antisense RNA.

The associated or conjugated substance may include hydrogels, proteins, carbohydrates, nucleic acids, and non-biological polymers such as plastics, metallic nanoparticles such as gold, silver and carbon nanostructures among others. Further examples of carrier systems include cellular systems (animal cells, plant cells, bacteria). Reactive dyes can be used to label groups at the cell surface, in cell membranes, organelles, or the cytoplasm.

These compounds can be linked to small molecules such as amino acids, vitamins, drugs, haptens, toxins, or environmental pollutants. Another important ligand is tyramine, where the conjugate is useful as a substrate for horseradish peroxidase. Additional embodiments are described in U.S. Patent Application Publication No. 2002/0077487.

Finally, these dyes are linked to hydrogels. Hydrogels may include collagen, gelatine, alginate, chitosan, PEGylated fibrinogen, PEG-dextran, aminopolysacharid, carboxymetylcellulose, acrylic, and poly(vinylpirrolidone) hydrogel among others.

Synthesis

The synthesis of the disclosed viscosity-sensitive reporter compounds typically is achieved in a multi-step reaction, starting with the synthesis of a methylene base followed by the reaction with squaric acid or a derivative of squaric acid. The synthesis of suitable methylene bases is either based on literature or novel methods. Generally, the spectral properties of the reporter compounds, including excitation and emission wavelengths for luminescent compounds, may be strongly dependent on the type of methylene base used. Typical starting materials include quarternized indolenines, benzthiazoles, benzoxazoles, benzimidazoles, among others. The synthesis of the squaraine-type compounds has been described in the following patents and patent application: U.S. Pat. No. 6,538,129, U.S. Pat. No. 7,250,517 and WO03/087052.

Overview of the Compositions

The compositions of the present disclosure may consist of one or more luminescent dye(s), wherein at least one luminescent dye is sensitive to the viscosity of the hydrogel. Additionally, linked dye(s) can be viscosity-insensitive or viscosity-sensitive. The other dye can also be sensitive to pH, temperature, hydrophilicity or to other parameters of environment. The compositions may include additional molecules such as photosensitizer, photosonic compound or photoacoustic compound useful for photodynamic therapy, photodynamic antimicrobial chemotherapy, or antimicrobial coating.

The compositions of the present disclosure can be covalently bound to the biological sample, hydrogel or any other substance with the aim to analyze the viscosity of the sample.

Hydrogels may include collagen, gelatine, alginate, chitosan, PEGylated fibrinogen, PEG-dextran, aminopolysacharid, carboxymetylcellulose, acrylic, and poly(vinylpirrolidone) hydrogel among others. Hydrogels can be environment-sensitive, e.g., sensitive to pH or temperature. Hydrogels can be formed either in-vitro or in-vivo. Alginate hydrogel can be formed in situ by injecting the hydrogel components (aqueous solution of alkali metal alginate and an aqueous solution of an alkali earth or transition metal ions) in a biological sample.

Overview of the Analysis Methods

Analysis of biological samples according to the present disclosure can be done by any methods which use luminescence as a read-out parameter. Different parameters of luminescence such as intensity, lifetime, polarization or their combination can be used. Analysis can be done by luminescence spectroscopy, luminescence imaging, luminescence microscopy and fluorescence lifetime imaging (FLIM) among others.

Luminescence can be excited with light (photoluminescence), ultrasound (sonoluminescence) or any other appropriate methods. Excitation light can be UV, visible, red, or near-infrared (NIR). Red and/or NIR excitation light may be advantageous due to generally lower intrinsic absorption and/or fluorescence at those wavelengths. Emission light can be UV, visible, red, or NIR. Red and/or NIR emission light may be advantageous due to generally lower intrinsic absorption and/or fluorescence at those wavelengths. Examples of excitation and/or emission ranges include 450-950 nm, 580-950 nm, 400-700 nm, 580-700 nm, and 250-1000 nm. Analysis can be done also in two-photon and multi-photon applications, super-resolution microscopy and luminescence tomography among others.

The analysis methods can be combined with medical treatment methods (e.g., theranostics).

EXAMPLES

Materials

Sodium alginate (medium viscosity) was from Sigma (A2033). Amine-reactive fluorescent dyes SeTau-405, SeTau-647, Seta-555 and Seta-650 (NHS esters) were from SETA BioMedicals. 4-Morpholineethanesulfonic acid, N-(3-dimetylaminopropyl)-N'-ethylcarbodiimide hydrochloride (EDC), N-hydroxysuccinimide (NHS), DIPEA, TSTU, and 1,6-diaminohexane were from Aldrich. Solvents were from Merck. All starting materials were used without further purification as purchased.

Absorption and emission spectra were measured in saline solutions at 25° C. in 1-cm standard quartz cells. The absorption spectra were recorded using a PerkinElmer Lambda 35 spectrophotometer and the emission spectra were taken using a Varian Cary Eclipse spectrofluorometer. The emission spectra were corrected.

Animal Experiments

The animal experiments were performed with male rats weighing 180-250 g. The research subject was superficial gluteal muscles (m. gluteus superficialis) and the myocardium.

Animal experiments were done in the Institute for Problems of Cryobiology and Cryomedicine of the National Academy of Sciences of Ukraine. All procedures involving the use and care of animals conform to the "Guide for the Care and Use of Laboratory Animals" published by the US National Institutes of Health (NIH Publication No. 85-23, revised 1996) and were approved by Stockholm Southern Ethics Review Board. The experimental protocols were approved by the Commission in Bioethics of the Institute for Problems of Cryobiology and Cryomedicine of the National Academy of Sciences of Ukraine.

Animals were maintained in the standard animal house conditions of 3 daily meals, at +20° C. air temperature and 65% humidity. Intraperitoneal ketamine anesthesia was applied in a dose of 75 mg/kg. For additional analgesia, nalbuphine was intramuscularly administered in 1 mg/kg dose. The animals were removed from the experiments by anesthetic overdosage.

Fluorescence Imaging

Luminescent images were taken using a Canon EOS 5D Mark II camera under constant matrix sensitivity (ISO-100), aperture and exposure (1 sec) or NIKON D610 camera at the constant matrix sensitivity (ISO-400), constant focus distance (85 mm), constant aperture, and constant exposure (4 s for red and orange channels and 20 s for green channel).

A brightness standard was prepared by the placing of 1-2 mm diameter piece of fluorescently labeled dense alginate that was injected into the animals on a black ruler. This brightness standard was placed at a small distance (1-3 cm) from the injected alginate before each image acquisition by the camera. To obtain the fluorescence signal, the sample (rat hip or heart) was illuminated at a distance of 10 cm using an LED equipped with a bandpass filter. A longpass filter placed in front of the camera lens was used to cutoff the excitation light. In case of the red-excitable, red-emitting dyes Seta-650 or Cy5 (red channel) a 636-nm 3 W LED, a 640/10 bandpass excitation filter and a 670 longpass emission filter were used. For the green-excitable, orange-emitting dyes 10 or Seta-555 (orange channel) a 530-nm 3 W LED, a 530/10 bandpass excitation filter and a 600-nm longpass emission filter was used. For the blue-excitable, green-emitting dye 9 (green channel) a 470-nm 3 W LED, a 470/10 bandpass excitation filter and a 546/20 bandpass emission filter were used.

The fluorescence images obtained in each channel were adjusted in such a way that the brightness standards on these images had equal brightness. Then the location of the fluorescence areas, which correspond to dense hydrogel (alginate) and its degradation products were determined and quantified (by area and brightness).

Example 1

3-Butoxy-4-(1,3,3-trimethyl-2,3-dihydro-1H-2-indolylidenmethyl)-3-cyclobutene-1,2-dione (1)

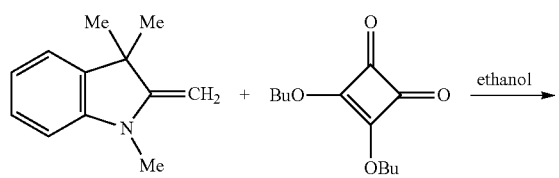

-continued

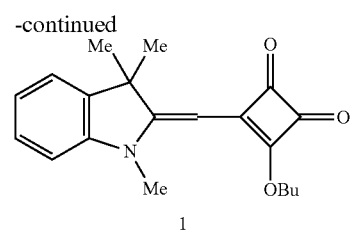

6.5 ml (36.8 mmol) of 1,3,3-trimethyl-2-methyleneindoline is added dropwise under argon to a solution of 8.4 ml (38.9 mmol) of 3,4-dibutoxy-3-cyclobutene-1,2-dione in 25 ml of ethanol. The mixture is stirred at room temperature for 1.5 hours and 3 hours at 40° C. Then it is left overnight for crystallization. The resulting yellow crystalline product is collected by filtration and washed with cooled ethanol. Yield: 10.1 g (84%). $^1$H-NMR (200 MHz, DMSO-d$_6$), δ, ppm: 7.42 (1H, arom., d, 7.3 Hz), 7.29 (1H, arom., t, 7.3 Hz), 7.17 (1H, arom., d, 7.5 Hz), 7.06 (1H, arom., t, 7.3 Hz), 5.32 (1H, CH, s), 4.80 (2H, OCH$_2$, t, 6.5 Hz), 3.39 (3H, NCH$_3$, s), 1.90-1.70 (2H, CH$_2$, m), 1.55 (6H, (CH$_3$)$_2$, s), 1.56-1.32 (2H, CH$_2$, m), 0.95 (3H, CH$_3$, t, 7.3 Hz). The structure 1 is confirmed also using the X-ray analysis. UV for the product 1: $\lambda_{max}$ (abs): 425 nm (ethanol).

Synthesis of 3-cyanoimino-2-(1,3,3-trimethyl-2,3-dihydro-1H-2-indolylidenmethyl)-4-(1,3,3-trimethyl-3H-2-indoliumylmethylene)-1-cyclobuten-1-olate triethylammonium salt (2)

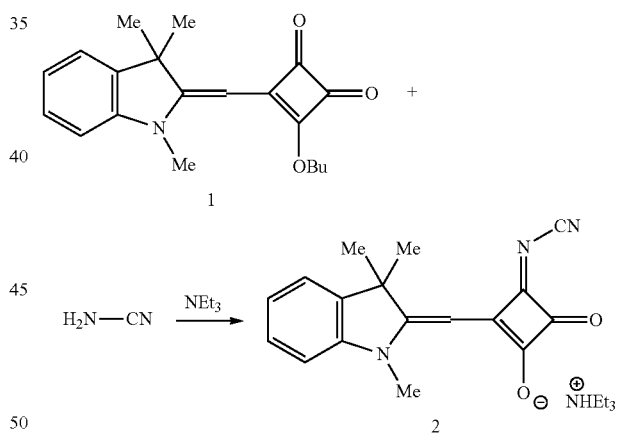

A mixture of 1 g (3.1 mmol) of 3-butoxy-4-(1,3,3-trimethyl-2,3-dihydro-1H-2-indolylidenmethyl)-3-cyclobutene-1,2-dione (1), 200 mg (4.8 mmol) of cyanamide and 0.5 ml (3.6 mmol) of triethylamine is refluxed with stirring in 10 ml of absolute ethanol for 12 h. The solvent is removed under reduced pressure by a rotary evaporator. The obtained gum is column purified (Silica gel 60, 0-5% methanol-chloroform) to give triethylammonium 3-cyanoimino-4-oxo-2-(1,3,3-trimethyl-2,3-dihydro-1H-2-indolylidenmethyl)-1-cyclobuten-1-olate (2) as an oiled yellow solid. Yield: 0.96 g (78%). $^1$H-NMR (300 MHz, DMSO-d$_6$), δ, ppm: 8.88 (1H, NH, broad s), 7.31 (1H, arom., d, 7.4 Hz), 7.20 (1H, arom., t, 7.8 Hz), 6.99 (1H, arom., d, 7.7 Hz), 6.91 (1H, arom., t, 7.3 Hz), 6.21 (0.5H, CH, broad s), 5.55 (0.5H, CH, broad s), 3.25 (3H, NCH$_3$, s), 3.10 (6H, N(C$\underline{H}_2$CH$_3$)$_3$, m), 1.56 (6H, (CH$_3$)$_2$, s), 1.18 (9H, N(CH$_2$CH$_3$)$_3$, t, 7.3 Hz). UV for product 2: λ$_{max}$ (abs) 435 nm (ethanol).

3,4-dioxo-2-(1,3,3-trimethyl-2,3-dihydro-1H-2-indo-lylidenmethyl)-1-cyclobutene-1-thiolate sodium salt (3)

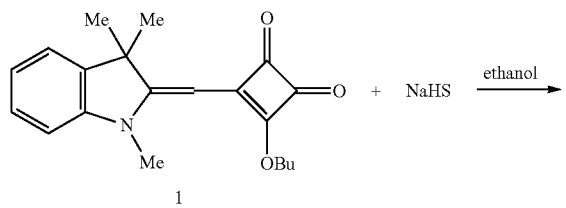

A mixture of 500 mg (1.54 mmol) of 3-butoxy-4-(1,3,3-trimethyl-2,3-dihydro-1H-2-indolylidenmethyl)-3-cyclobutene-1,2-dione (1) and 250 mg (4.46 mmol) of sodium hydrosulfide is refluxed with stirring for 4 hours in 20 ml of absolute ethanol. The reaction mixture is cooled in a refrigerator and sodium 3,4-dioxo-2-(1,3,3-trimethyl-2,3-dihydro-1H-2-indolylidenmethyl)-1-cyclobutene-1-thiolate (3) is collected by filtration and washed with ethanol. Yield: 250 mg (53%) as orange-yellow crystals. $^1$H-NMR (200 MHz, DMSO-d$_6$), δ, ppm: 7.28 (1H, arom., d, 7.5 Hz), 7.19 (1H, arom., td, 7.5, 1.2 Hz), 6.94 (1H, arom., d, 7.9 Hz), 6.89 (1H, arom., t, 7.4 Hz), 5.82 (1H, CH, s), 3.27 (3H, NCH$_3$, s), 1.57 (6H, (CH$_3$)$_2$, s). UV for product 3: λ$_{max}$ (abs): 445 nm (ethanol).

3-dicyanomethylene-4-oxo-2-(1,3,3-trimethyl-2,3-dihydro-1H-2-indolylidenmethyl)-1-cyclobuten-1-olate triethylammonium salt (4)

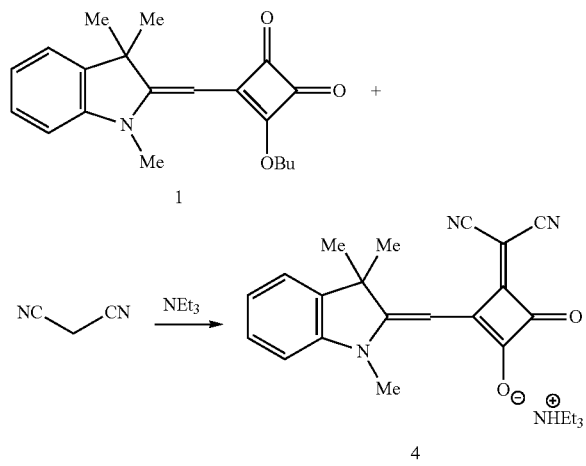

1 ml (7.14 mmol) of triethylamine is added dropwise to a mixture of 2 g (6.15 mmol) of 3-butoxy-4-(1,3,3-trimethyl-2,3-dihydro-1H-2-indolylidenmethyl)-3-cyclobutene-1,2-dione (1), 440 mg (6.66 mmol) of malononitrile, 35 ml of ethanol and stirred for 5.5 hours at room temperature. The solvent is removed under reduced pressure by a rotary evaporator. The raw product is column purified (Silica gel 60, 0-2% methanol-chloroform) to give triethylammonium 3-dicyanomethylene-4-oxo-2-(1,3,3-trimethyl-2,3-dihydro-1H-2-indolylidenmethyl)-1-cyclobuten-1-olate (4) as orange crystals. Yield is 98%. $^1$H-NMR (200 MHz, DMSO-d$_6$), δ, ppm: 8.74 (1H, NH, broad s), 7.29 (1H, arom., d, 7.5 Hz), 7.20 (1H, arom., t, 7.5 Hz), 6.95 (1H, arom., d, 8.3 Hz), 6.93 (1H, arom., t, 7.8 Hz), 5.92 (1H, CH, s), 3.25 (3H, NCH$_3$, s), 3.11 (6H, N(CH$_2$CH$_3$)$_3$, q, 7.3, 14.6 Hz), 1.59 (6H, (CH$_3$)$_2$, s), 1.20 (9H, N(CH$_2$CH$_3$)$_3$, t, 7.3 Hz). The structure of compound 4 was confirmed by X-ray analysis. UV for product 4: λ$_{max}$ (abs): 460 nm (ethanol).

2-[3-hydroxy-4-oxo-2-(1,3,3-trimethyl-2,3-dihydro-1H-2-indolylidenmethyl)-2-cyclobutenyliden]-1,3-indanedione (5)

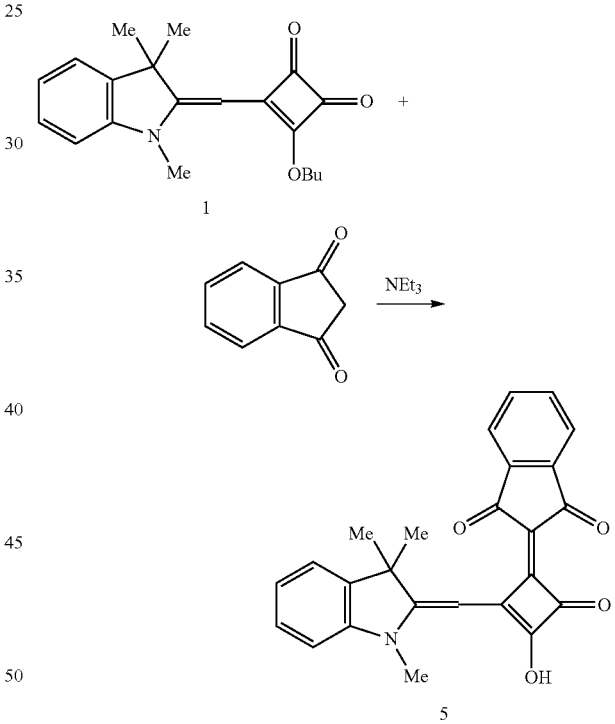

0.2 ml (1.42 mmol) of triethylamine is added dropwise to a mixture of 250 mg (0.77 mmol) of 3-butoxy-4-(1,3,3-trimethyl-2,3-dihydro-1H-2-indolylidenmethyl)-3-cyclobutene-1,2-dione (1), 115 mg (0.79 mmol) of 1,3-indanedione, and 10 ml of ethanol. Solution color is darkened during this time and intense orange-brown solution is obtained. The mixture is stirred for 1 hour at room temperature and refluxed for 4 h. The solvent is removed under reduced pressure by a rotary evaporator. The raw product is column purified (Silica gel 60, 0-20% methanol-dichloromethane) to give 2-[3-hydroxy-4-oxo-2-(1,3,3-trimethyl-2,3-dihydro-1H-2-indolylidenmethyl)-2-cyclobutenyliden]-1,3-indanedione (5). Yield: 120 mg (39%). R$_f$ 0.31 (Sorbfil, chloroform-methanol, 10:1). $^1$H-NMR (300 MHz, DMSO-d$_6$), δ, ppm: 7.55-7.30 (6H, arom., m), 7.23 (1H, arom., t, 7.8 Hz), 7.02 (1H, arom., d, 7.3 Hz), 6.96 (1H, arom., t, 7.3 Hz), 3.43 (3H, NCH$_3$, s), 1.61 (6H, (CH$_3$)$_2$, s). UV for product 5: λ$_{max}$ (abs): 490 nm (ethanol).

3-Butoxy-4-(3-methyl-2,3-dihydro-1,3-benzothiazol-2-ylidenmethyl)-3-cyclobutene-1,2-dione (6)

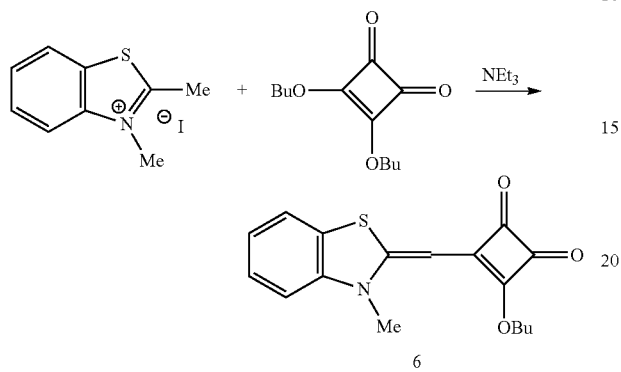

0.3 ml (2.1 mmol) of triethylamine is added dropwise to a mixture of 0.5 g (1.7 mmol) of 2,3-dimethyl-1,3-benzothiazol-3-ium iodide, 0.4 ml (1.85 mmol) of 3,4-dibutoxy-3-cyclobutene-1,2-dione, 15 ml of ethanol and then refluxed for 2 h. A by-product is isolated by a filtration of the hot solution. The filtrate is cooled in a refrigerator and the crystalline product is collected by filtration and washed with ethanol. Yield: 490 mg (91%). $^1$H-NMR (200 MHz, DMSO-d$_6$), δ, ppm: 7.77 (1H, arom., d, 7.8 Hz), 7.45 (1H, arom., dd, 8.2, 1.5 Hz), 7.40 (1H, arom., td, 8.3, 1.2 Hz), 7.21 (1H, arom., app. t, 7.0 Hz), 5.52 (1H, CH, s), 4.73 (2H, OCH$_2$, t, 6.6 Hz), 3.62 (3H, NCH$_3$, s), 1.80 (2H, CH$_2$, m), 1.45 (2H, CH$_2$, m), 0.95 (3H, CH$_3$, t, 7.4 Hz). UV for product 6: λ$_{max}$ (abs): 440 nm (ethanol).

3-dicyanomethylene-2-(3-methyl-2,3-dihydro-1,3-benzothiazol-2-yliden methyl)-4-oxo-1-cyclobuten-1-olate triethylammonium salt (7)

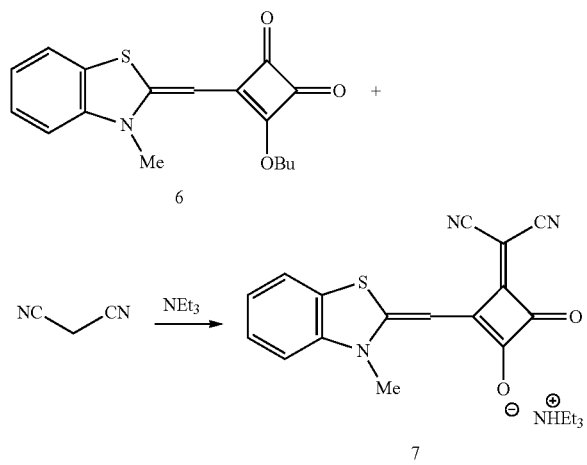

0.15 ml (1.07 mmol) of triethylamine is added dropwise to a mixture of 0.2 g (0.63 mmol) of 3-butoxy-4-(3-methyl-2,3-dihydro-1,3-benzothiazol-2-ylidenmethyl)-3-cyclobutene-1,2-dione (6), 42 mg (0.63 mmol) of malononitrile and 10 ml of ethanol. This is stirred for 2 hours at room temperature and 5 hours at 50° C. The solvent is removed under reduced pressure by a rotary evaporator. The raw product is column purified (Silica gel 60, 0-5% methanol-chloroform) to give triethylammonium 3-dicyanomethylene-2-(3-methyl-2,3-dihydro-1,3-benzothiazol-2-ylidenmethyl)-4-oxo-1-cyclobuten-1-olate (7). Yield: 190 mg (69%). $^1$H-NMR (200 MHz, DMSO-d$_6$), δ, ppm: 8.82 (1H, NH, broad s), 7.61 (1H, arom., d, 8.0 Hz), 7.29 (1H, arom., td, 7.7, 1.3 Hz), 7.23 (1H, arom., dd, 8.0, 0.9 Hz), 7.06 (1H, arom., td, 7.1, 1.6 Hz), 5.88 (1H, CH, s), 3.43 (3H, NCH$_3$, s), 3.10 (6H, N(CH$_2$CH$_3$)$_3$, q, 7.3, 14.6 Hz), 1.20 (9H, N(CH$_2$CH$_3$)$_3$, t, 7.4 Hz). Element analysis: N (found)=13.35%, N (calcd)=13.71%.

1-(5-carboxypentyl)-2-(4-dicyanomethylene-2-olato-3-oxo-1-cyclobutenyl methylene)-3,3-dimethyl-5-indolinesulfonate triethylammonium salt (9)

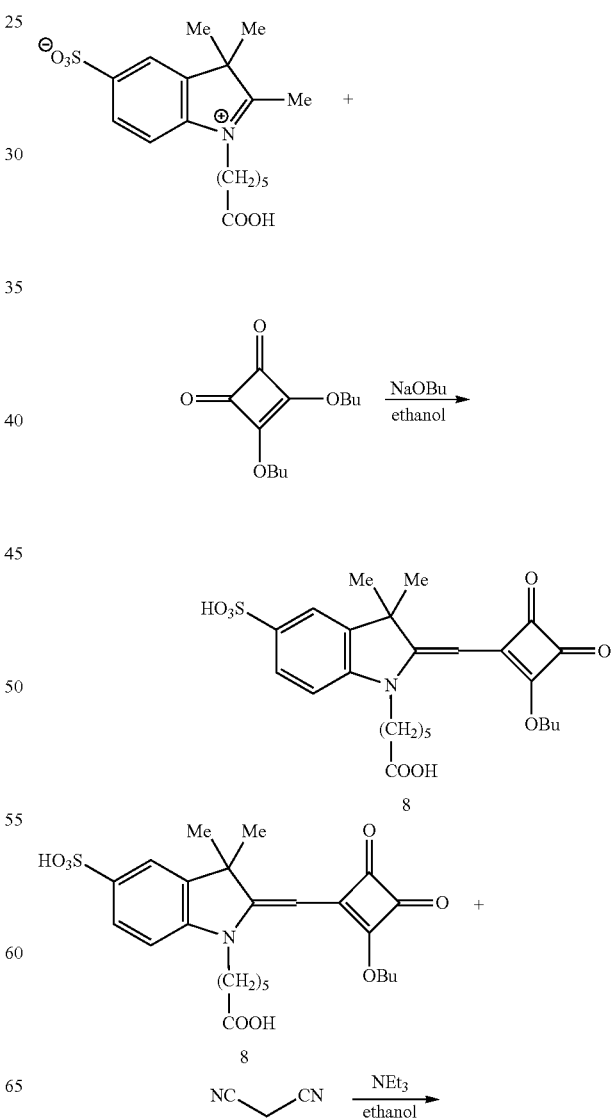

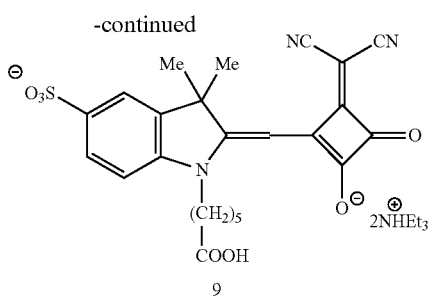

9

Sodium butylate obtained from 27 mg of sodium and 0.5 ml of absolute 1-butanol is added dropwise to an ice bath cooled suspension of 0.6 g (1.13 mmol) of 1-(5-carboxypentyl)-2,3,3-trimethyl-3H-5-indoliumsulfonate containing 35% KBr as an impurity, 300 mg (1.32 mmol) of 3,4-dibutoxy-3-cyclobutene-1,2-dione in 24 ml of absolute 1-butanol. Then the mixture is stirred at room temperature for 1 hour and 2.5 hours at 45-50° C. The solvent is removed under reduced pressure by a rotary evaporator to give raw product 8.

0.2 ml (1.42 mmol) of triethylamine is added dropwise to a mixture of dried 8, 75 mg (1.14 mmol) of malononitrile, 20 ml of ethanol and stirred for 2 hours at room temperature and then left for two days. The solvent is removed and the raw product is column purified (LiChroprep RP-18, methanol-water, 2:5 v/v)) to give product 9. Yield: 180 mg (23%). $^1$H-NMR (200 MHz, DMSO-$d_6$), δ, ppm: 8.87 (2H, NH, broad s), 7.50 (1H, arom., s), 7.49 (1H, arom., d, 6.3 Hz), 6.88 (1H, arom., d, 6.8 Hz), 5.92 (1H, CH, s), 3.83-3.62 (2H, NCH$_2$, broad s), 3.11 (12H, N(C$\underline{H}_2$CH$_3$)$_3$, m), 2.18 (2H, CH$_2$COOH, t, 7.1 Hz), 1.57 (6H, (CH$_3$)$_2$, s), 1.73-1.27 (6H, m), 1.19 (18H, N(CH$_2$C$\underline{H}_3$)$_3$, t, 7.3 Hz). FAB-MS (in glycerol): (MH$^+$) for $C_{36}H_{53}N_5O_7S$ calculated 699.9. found 700. UV for product 9: $\lambda_{max}$ (abs): 470 nm (water).

2-[(3,4-bis(dicyanomethylene)-2-oxidocyclobut-1-en-1-yl)methylene]-1-(5-carboxy pentyl)-3,3-dimethylindoline-5-sulfonate (10)

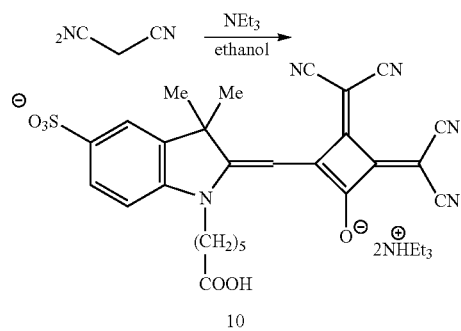

8

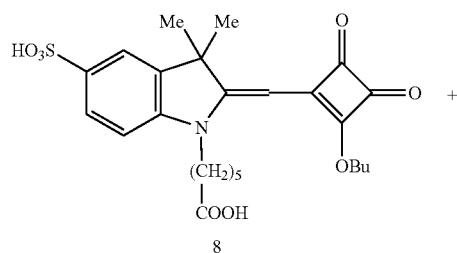

10

1.0 ml (7.16 mmol) of triethylamine is added dropwise to a mixture of dried 300 mg (0.59 mmol) of 8, 100 mg (1.51 mmol) of malononitrile, 20 ml of ethanol and stirred for 2 hours at room temperature. The solvent is removed and the residue is hydrolyzed by refluxing in 10 mL of 0.2N HCl for an hour. The raw product is column purified (LiChroprep RP-18, acetonitrile-water, 1:5 v/v)) to give product 10. Yield: 43 mg (10%). $^1$H-NMR (200 MHz, DMSO-$d_6$), δ, ppm: 9.00-8.80 (2H, NH, broad s), 7.59 (1H, arom., s), 7.55 (1H, arom., d, 8.6 Hz), 7.12 (1H, arom., d, 7.1 Hz), 6.03 (1H, CH, s), 3.95-3.77 (2H, NCH$_2$, broad s), 3.18-2.99 (12H, N(C$\underline{H}_2$CH$_3$)$_3$, m), 2.17 (2H, CH$_2$COOH, t, 6.9 Hz), 1.56 (6H, (CH$_3$)$_2$, s), 1.79-1.26 (6H, m), 1.17 (18H, N(CH$_2$C$\underline{H}_3$)$_3$, t, 7.2 Hz). UV for product 10: $\lambda_{max}$ (abs): 559 nm (water).

Squaraine Dye NHS Ester 11

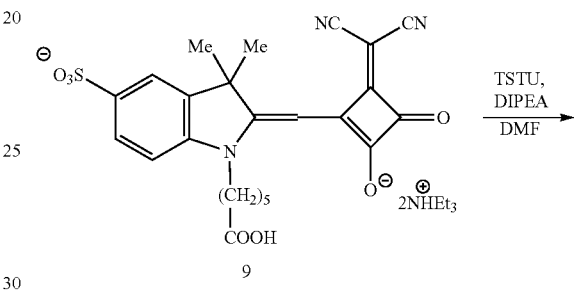

9

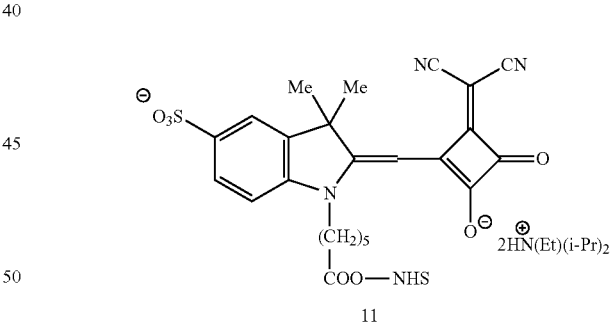

11

56 mg (0.08 mmol) of the dye 9 were dissolved in 3 mL of anhydrous DMF. Then 36 mg (0.12 mmol) of TSTU and 100 μL of DIPEA were added and the mixture was stirred at room temperature for 1 h. The reaction was monitored by TLC (RP-18, water-acetonitrile=2:1, v/v). The product was precipitated with ether and then column purified (LiChroprep RP-18, acetonitrile-water, 1:5.5 v/v)) to give NHS ester 11. Yield: 36 mg (52%). $^1$H-NMR (200 MHz, DMSO-$d_6$), δ, ppm: 8.36-8.05 (2H, NH, broad s), 7.47 (1H, arom., s), 7.45 (1H, arom., d, 6.2 Hz), 6.89 (1H, arom., d, 7.9 Hz), 5.90 (1H, CH, s), 3.80-3.50 (6H, m), 3.24-3.04 (4H, m), 2.80 (4H, CH, s), 2.64 (2H, CH$_2$COOH, t, 7.3 Hz), 1.55 (6H, (CH$_3$)$_2$, s), 1.77-1.34 (6H, m), 1.31-1.16 (30H, C$\underline{H}_3$ (DIPEA), m). UV for product 11: $\lambda_{max}$ (abs): 470 nm (water).

Squaraine Dye NHS Ester 12

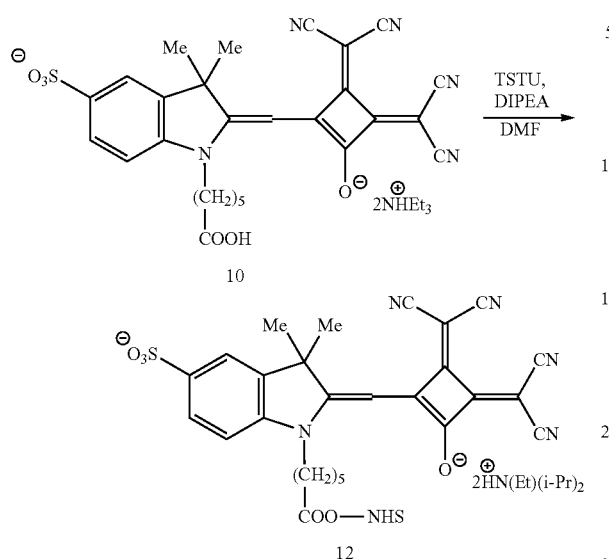

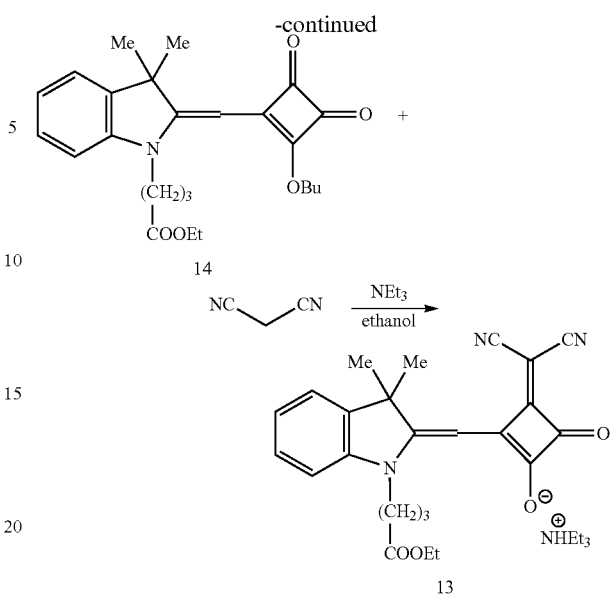

10 mg (13 µmol) of the dye 10 were dissolved in 1 mL of anhydrous DMF. Then 5 mg (16 µmol) of TSTU and 30 µL of DIPEA were added and the mixture was stirred at room temperature for 1 h. The reaction was monitored by TLC (RP-18, water-acetonitrile=2:1, v/v). The product was precipitated with ether, dried and then column purified (LiChroprep RP-18, acetonitrile-water, 1:5 v/v)) to give NHS ester 12. Yield: 6 mg (54%). UV for product 12: $\lambda_{max}$ (abs): 559 nm (water).

Triethylammonium 3-dicyanomethylene-2-[1-(3-ethyloxycarbonylpropyl)-3,3-dimethyl-2,3-dihydro-1H-2-indolylidenmethyl]-4-oxo-1-cyclobuten-1-olate (13)

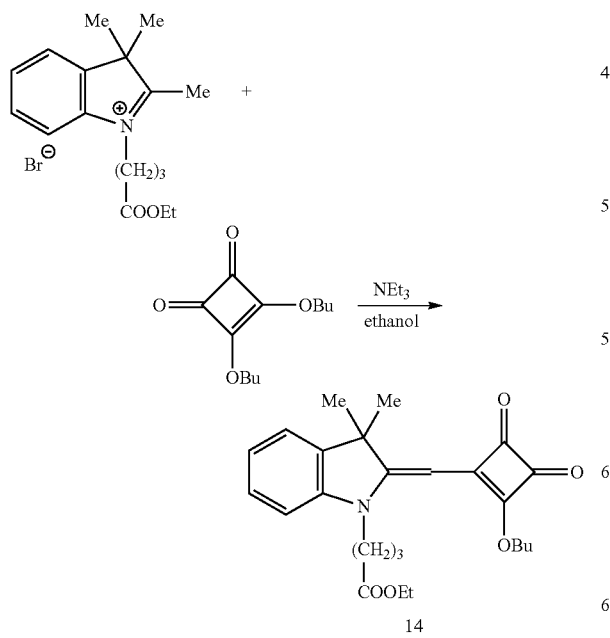

0.6 mL (4.28 mmol) of triethylamine was added dropwise to a mixture of 1 g (2.82 mmol) of 1-(3-ethyloxycarbonylpropyl)-2,3,3-trimethyl-3H-indolium bromide, 0.65 mL (3.01 mmol) of 3,4-dibutoxy-3-cyclobutene-1,2-dione in 15 mL of ethanol and stirred for 10 h at room temperature. The solvent was removed under reduced pressure and the raw product was purified by column chromatography (Silica gel 60, 0-0.7% methanol-dichloromethane) to give (810 mg, 68%) ethyl 4-[2-(2-butoxy-3,4-dioxo-1-cyclobutenyl-methylene)-3,3-dimethyl-2,3-dihydro-1H-1-indolyl]butanoate (14) as orange crystals. A mixture of 500 mg (1.18 mmol) of 14, 130 mg (1.97 mmol) of malononitrile and 0.23 mL (1.64 mmol) of triethylamine in 20 mL of ethanol was stirred at room temperature for 10 h. The solvent was removed under reduced pressure and the residue was purified by column chromatography (Silica gel 60, 0-10% methanol-chloroform). Yield of 13: 600 mg (98%) as a very viscous solid. UV/Vis, $\lambda_{max}$ (abs): 465 nm (EtOH). $^1$H-NMR (200 MHz, DMSO-$d_6$), δ, ppm: 9.12-8.52 (1H, broad s, N$\underline{H}^+$), 7.33 (1H, d, 7.1 Hz, arom.), 7.22 (1H, td, 7.6, 1.1 Hz, arom.), 6.98 (1H, d, 7.6 Hz, arom.), 6.94 (1H, t, 7.8, 1.0 Hz, arom.), 5.91 (1H, s, C$\underline{H}$), 4.03 (2H, q, 7.1, 14.2 Hz, COOC$\underline{H}_2$CH$_3$), 3.76 (2H, t, 7.4 Hz, NC$\underline{H}_2$), 3.10 (6H, q, 7.3, 14.6 Hz, N(C$\underline{H}_2$CH$_3$)$_3$), 2.40 (2H, t, 7.4 Hz, C$\underline{H}_2$COOH), 1.93 (2H, m, C$\underline{H}_2$), 1.57 (6H, s, C(C$\underline{H}_3$)$_2$), 1.17 (9H, t, 7.3 Hz, N(CH$_2$C$\underline{H}_3$)$_3$), 1.16 (3H, t, 7.1 Hz, COOCH$_2$C$\underline{H}_3$).

Example 2

Preparation of Amino-Modified Sodium Alginate 2.0 g of sodium alginate (Alg) was dissolved in 200 mL of 50 mM MES buffer pH 6.1. The MES buffer was prepared by dissolving 9.8 g of 4-morpholineethanesulfonic acid in 1 L water and then the pH was adjusted to pH 6.1 using concentrated sodium hydroxide. With constant stirring to a solution of alginate were added 930 mg of N-(3-dymetylaminopropyl)-N'-ethylcarbodiimide hydrochloride (EDC) and 310 mg of N-hydroxysuccinimide (NHS). After 30 minutes, 2 g of 1,6-diaminohexane were added to the reaction mixture and stirred for 12 hours. To remove residual 1,6-diaminohexane, the resulted amino-modified sodium alginate was precipitated with isopropanol, filtered, washed with isopropanol, and dried. Yield: 2.03 g.

Example 3

Labeling of Sodium Alginate with Cyanine Dye Cy5

Figure 2:
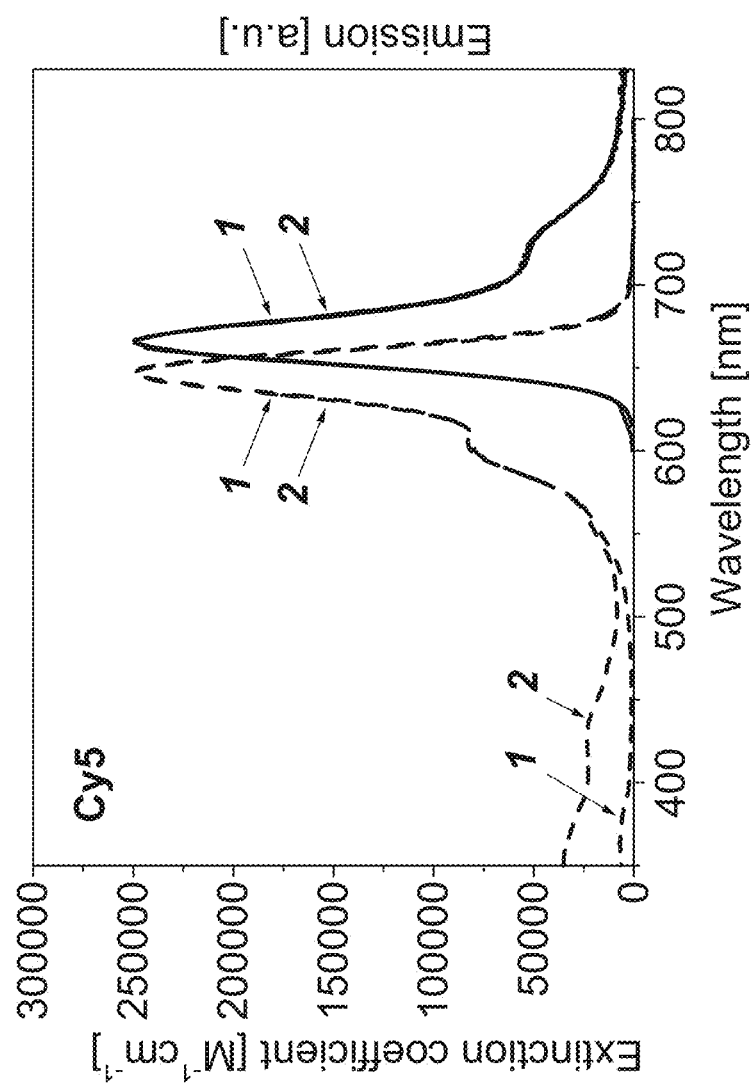
FIG. 2 Absorption (dashed line) and emission (solid line) of Cy5 free in saline solution (1) and after binding to non-gelated alginate (2), λ (ex)=600 nm (see Example 3).

525 mg of amino modified sodium alginate, synthesized as described in Example 2 was dissolved in 70 mL of 50 mM bicarbonate buffer pH 9.0. A solution of 9.0 mg of cyanine dye Cy5 (NHS ester) (GE Healthcare) in 1 mL of distilled water was added and the mixture was stirred for 2 hours. Then labeled alginate was precipitated with 170 mL isopropanol, filtered and washed with isopropanol. Yield: 521 mg. $\lambda_{max}$ (abs)=647 nm, $\lambda_{max}$(em)=666 nm in aqueous solution (FIG. 2).

Example 4

Labeling of Sodium Alginate with Squaraine Dye 9

Figure 3:
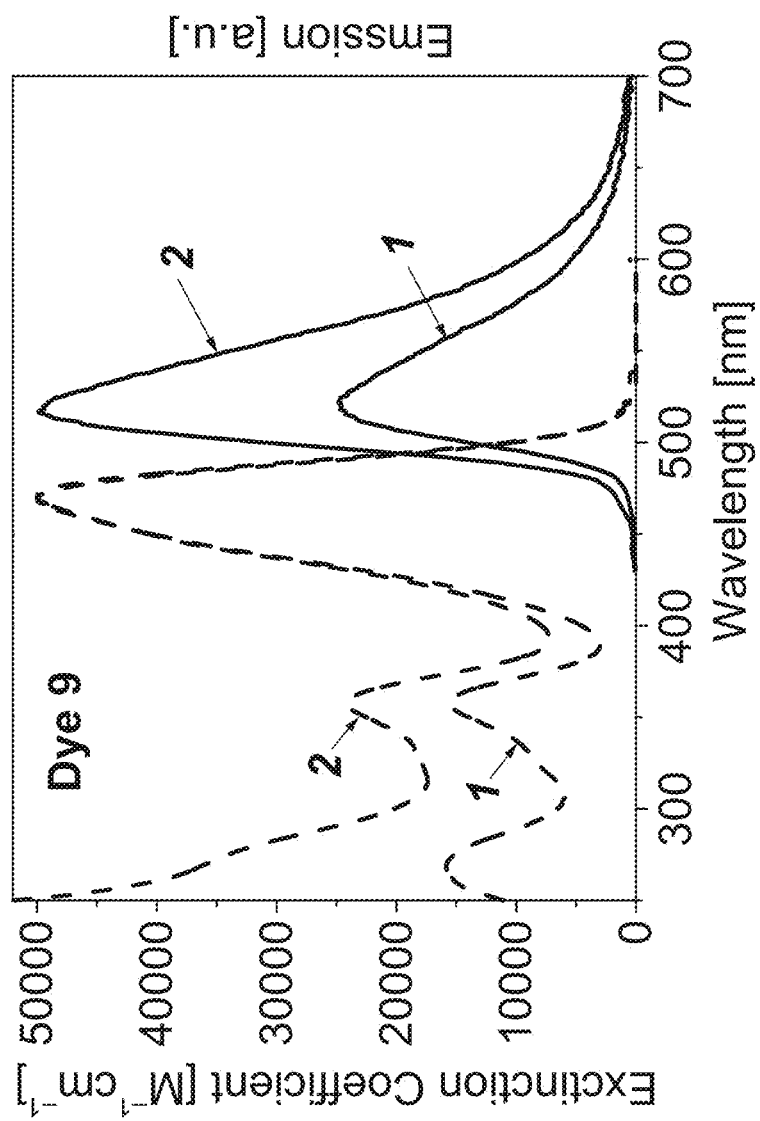
FIG. 3 Absorption (dashed line) and emission (solid line) of Dye 9 free in saline solution (1) and after binding to non-gelated alginate (2), λ (ex)=470 nm (see Example 4).

500 mg of amino modified sodium alginate (Example 2) was dissolved in 55 mL of 50 mM bicarbonate buffer pH 9.0. A solution of 7.0 mg of cyanine dye 11 (9-NHS ester) in 1 mL of DMF was added and the mixture was stirred for 12 hours. Then dye labeled alginate was precipitated with 170 mL of isopropanol, filtered and washed with isopropanol on the filter. Yield: 450 mg. $\lambda_{max}$ (abs)=470 nm, $\lambda_{max}$(em)=519 nm in aqueous solution (FIG. 3).

Example 5

Labeling of Sodium Alginate with Squaraine Dye 10

Figure 4:
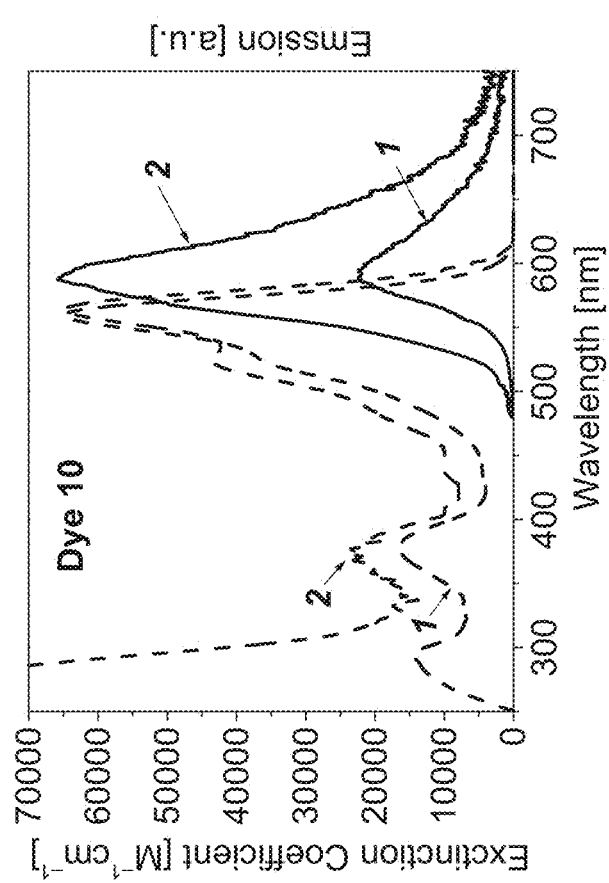
FIG. 4 Absorption (dashed line) and emission (solid line) of Dye 10 free in saline solution (1) and after binding to non-gelated alginate (2), λ (ex)=530 nm (see Example 5).

200 mg of amino modified sodium alginate (Example 2) was dissolved in 25 mL of 50 mM bicarbonate buffer pH 9.0. A solution of 2.0 mg of cyanine dye 12 (10-NHS ester) in 0.3 mL of DMF was added and the mixture was stirred for 12 hours. The labeled alginate was precipitated with 170 mL of isopropanol, filtered and washed with isopropanol. Yield: 183 mg. $\lambda_{max}$ (abs)=558 nm, $\lambda_{max}$(em)=588 nm in aqueous solution (FIG. 4).

Example 6

Labeling of Sodium Alginate with Viscosity-Sensitive Dye 9 and Viscosity-Insensitive Dye Seta-650 or Cy5

Figure 5:
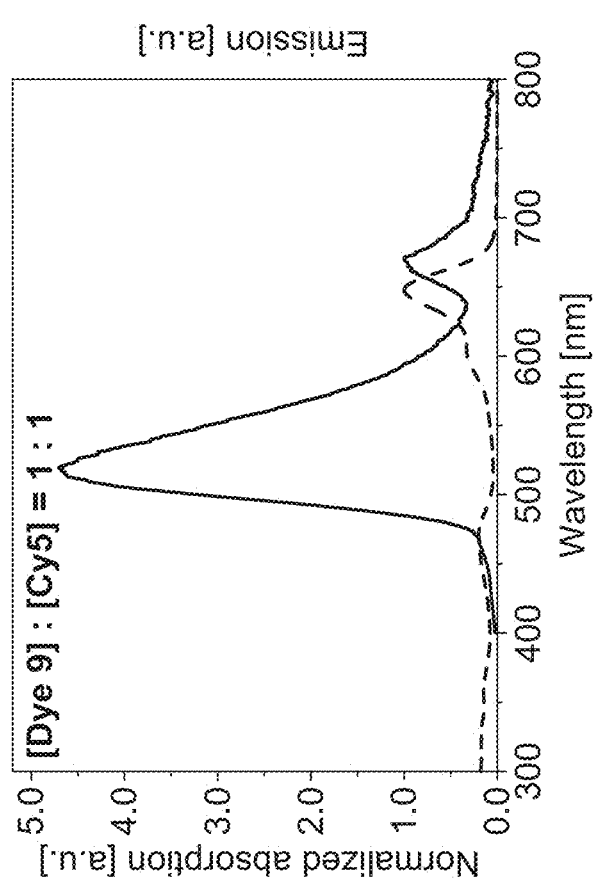
FIG. 5 Absorption (dashed line) and emission (solid line) of non-gelated alginate in saline solution labeled with Dye 9 and Cy5 at a molar ratio [Dye 9]:[Cy5]=1:1, λ (ex)=470 nm (see Example 6).

To a solution of 270 mg of amino-modified sodium alginate in 15 mL of 50 mM bicarbonate buffer pH 9.0 was added a solution of 6.0 mg of 9-NHS ester and 5.0 mg of Seta-650-NHS ester (SETA BioMedicals) or Cy5 (GE Healthcare) in 1 mL of DMF. The resulting solution was stirred for 2 hours at room temperature; the dye labeled alginate was precipitated with 50 mL of isopropanol, filtered, washed with isopropanol, and dried. Yield of the luminescently labeled alginate was 240 mg for 9-Seta-650-Alg and 215 mg for 9-Cy5-Alg. The molar ratio of the dyes [9]:[Seta-650] and [9]:[Cy5] covalently bound to the alginate (1:1) was calculated using their molar absorptivities (E) 50,000 $M^{-1}$ $cm^{-1}$ (9) and 210,000 $M^{-1}$ $cm^{-1}$ (Seta-650) or 250,000 $M^{-1}$ $cm^{-1}$ (Cy5). $\lambda_{max}$ (abs)=469, 651 nm (9-Seta-650-Alg) or 469, 647 nm (9-Cy5-Alg); $\lambda_{max}$ (em)= 518, 671 nm (9-Seta-650-Alg) or 518, 667 nm (9-Cy5-Alg) (measured in water, $\lambda$ (ex)=470 nm) (FIG. 5).

Example 7

Labeling of Sodium Alginate with Dyes 10 and Seta-650 or Cy5

Figure 6:
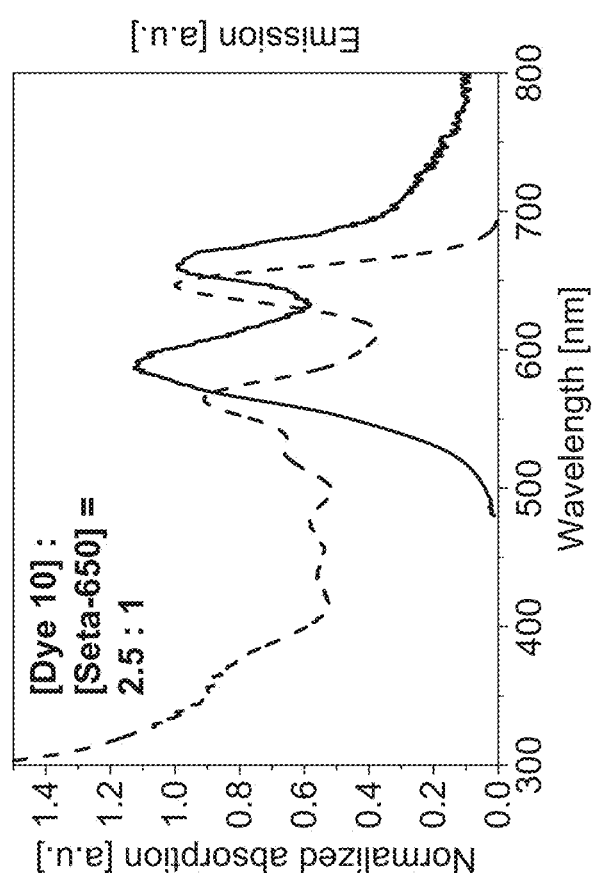
FIG. 6 Absorption (dashed line) and emission (solid line) of non-gelated alginate in saline solution stained with Dye 10 and Seta-650 dye at a molar ratio [Dye 10]:[Seta-650 dye]=2.5:1, λ (ex)=530 nm (see Example 7).

To a solution of 150 mg of amino-modified sodium alginate in 8.5 mL of 50 mM bicarbonate buffer pH 9.0 was added a solution of 2.5 mg of 10-NHS ester and 2.7 mg of Seta-650-NHS ester or Cy5 in 0.5 mL DMF. The resulting solution was stirred for 3 hours at room temperature; the dye labeled alginate was precipitated with 30 mL of isopropanol, filtered, washed with isopropanol, and dried. Yield of 10-Seta-650 (Cy5)-Alg: 149 mg. The molar ratio of the dyes [10]:[Seta-650] and [10]:[Cy5] covalently bound to alginate (2.5:1) was calculated using their molar absorptivities ($\epsilon$) 65,000 $M^{-1}cm^{-1}$ (9) and 210,000 $M^{-1}$ $cm^{-1}$ (Seta-650) or 250,000 $M^{-1}$ $cm^{-1}$ (Cy5). $\lambda_{max}$ (abs)=565, 651 nm (9-Seta-650-Alg) or 565, 647 nm (9-Cy5-Alg); $\lambda_{max}$(em)=591, 671 nm (9-Seta-650-Alg) or 591, 667 nm (9-Cy5-Alg) (measured in water, $\lambda$ (ex)=530 nm) (FIG. 6).

Example 8

Labeling of Sodium Alginate with Fluorescein

Amino-modified sodium alginate (350 mg) (Example 2) was dissolved in 45 mL of 50 mM bicarbonate buffer pH 9.0. A solution of 5.1 mg of Fluorescein isothiocyanate (FITC) in 1 mL of DMF was added and stirred for 2 hours. Then the dye labeled alginate was precipitated with isopropanol, filtered and washed with isopropanol on the filter. Yield: 195 mg. $\lambda_{max}$ (abs)=492 nm, $\lambda_{max}$(em)=513 nm (measured in water).

Example 9

Labeling of Sodium Alginate with SeTau-405 Dye (SETA BioMedicals)

Aminomodified sodium alginate (250 mg) (Example 2) was dissolved in 33 mL of 50 mM bicarbonate buffer pH 9.0. A solution of 5.1 mg dye SeTau-405-NHS in 1.5 ml DMF was added and stirred for 2 hours. Then dye labeled alginate was precipitated with isopropanol, filtered and washed with isopropanol on the filter. Yield: 248 mg. $\lambda_{max}$ (abs)=395 nm; $\lambda_{max}$(em)=519 nm.

Example 10

Labeling of Chitosan with Viscosity-Sensitive Dye 9

To a solution of 25 mg of dye 9 in 0.5 mL of 50 mM MES buffer (pH 6.1) was consistently added 8 mg of N-(3-dimetylaminopropyl)-N'-ethylcarbodiimid hydrochloride (EDC) and 4 mg of N-hydroxysuccinimide (NHS). The mixture was stirred for 30 minutes (Solution 1). Then 500 mg of low molecular weight chitosan (75-85% deacetylated, Sigma-Aldrich) was dissolved in 50 mL of 0.1 M acetic acid (Solution 2). To chitosan solution (solution 2) was added dropwise under stirring to the solution 1 and stirred at room temperature for 12 hours. Chitosan, luminescently labeled with dye 9, was precipitated with 100 mL of acetone, filtered and washed with acetone and isopropanol on the filter. Yield: 465 mg.

Example 11

Implantation of Luminescently Labeled Alginate Hydrogel into Rat Hip Muscle

The rat under ketamine anesthesia was placed on a surgical table. After pretreatment of the surgical area (shaving hair and antiseptic treatment) a longitudinal incision through the skin was made and the wound was opened using forceps.

A mixture of 0.04 mL of 10% calcium gluconate solution (CaGluc) and 0.05 mL of 1.0-1.5% fluorescently labeled sodium alginate in saline solution were carefully filled in a syringe without mixing. A needle with a 20° bevel tip was inserted at a ~20° angle into the m. gluteus superficialis (heel up) and the entire solution in the syringe was injected to the required depth of 1 mm. To prevent leakage of the injected solution, the needle was removed from the muscle with a delay of 4-5 s after the injection. Interaction of sodium alginate with calcium gluconate in the muscle results in the in situ formation of a fluorescently labeled, dense alginate implant. Subsequently the fluorescence images were taken to get a zero time point and the edges of the wound were closed.

An opposite limb was intramuscularly injected with nalbuphine of 1 mg/kg of body weight. The rat was placed into the recovery room. For obtaining the time-dependent alginate hydrogel behavior the rats were administered with anesthesia and skin sutures were re-opened before taking an image. After taking the images the wound was treated with an antiseptic (0.5% chlorhexidine in 70% aq. ethanol) and the skin was re-sutured.

Example 12

In-Vivo Preparation of Luminescently Labeled Alginate Hydrogel in Rat Myocardium The rat under ketamine anesthesia was placed on a surgical table. After pretreatment of a surgical area (shaving hair and antiseptic treatment) a thoracotomy at the intercostal space between the 4th and 5th rip was performed and the heart of the live rat was exteriorized.

0.03 mL of 10% calcium gluconate solution and then 0.03 mL of 0.5-1% fluorescently labeled sodium alginate in saline solution were carefully filled into a syringe without mixing the solutions. A needle with 20° bevel tip was inserted at a ~20° angle into left ventricular myocardium and the entire solution in the syringe was rapidly injected to a required depth of 1 mm. The injection was done immediately after the heart was temporarily removed from the chest cavity. To prevent leakage of the injected solution, the needle was removed from the myocardium with a delay of 4-5 s after the injection. The interaction of sodium alginate with calcium gluconate in the tissue results in the in situ formation of a fluorescent dense alginate implant.

Then the heart was either removed and the animal was euthanized to get a zero time data point or it was placed back into the chest cavity of the rat for the next measurement and the wound was closed. For an animal's anesthesia nalbuphine was intramuscularly injected into a rat hip in a dose of 1 mg/kg of body weight. At a specific time after the gel injection the test animals were euthanized with a ketamine overdose and the hearts were removed and frozen.

Example 13

In-Vivo Preparation of Luminescently Labeled Chitosan Implant 200 mg of chitosan, luminescently labeled with a luminescent dye were dissolved in 8 mL of phosphate buffer saline (PBS), containing 5.4 mL of acetic acid. At 8-12° C. the obtained chitosan solution was added dropwise to a solution of 1.9 g of beta-glycerol phosphate disodium salt in 2 mL of PBS. The obtained solution was filtered through a 0.22 micron membrane filter. The filtered solution (0.06-0.10 mL) was loaded into the syringe and injected to the required depth into the biological tissue. Warming of the luminescently labeled chitosan solution to body temperature leads to the in-situ formation of a dense implant in the biological tissue.

Example 14

In-Vitro Preparation of a Luminescently Labeled Alginate Implant

A fluorescently labeled sodium alginate (0.5 g) was dissolved in 4.5 mL saline solution. The mixture was stirred with a mechanical stirrer to speed up the process and subsequent swelling of the polymer gel. After obtaining a homogeneous gel, it is kept in the ultrasonic bath (40 kHz) for several hours at 40-50° C. for homogenization and release of air bubbles. The gel was transferred to a metal, glass or polymer container, which has the desired shape of the future implant, and then left for 1 day to obtain a shaped gel. The resulting implant was stored at 3-5° C. Before using the implant it was sterilized for 20 minutes at 110-115° C. in a steam sterilizer. Our used implant had the shape of a cylindrical tablet with a diameter of 0.5 cm and a height of 0.25 cm.

Example 15

Introduction of the Luminescently Labeled Alginate Implant in a Rat Hip Muscle by Surgical Transplantation The animal, which had undergone ketamine anesthesia, was placed on a surgical table. After pretreatment of the surgical field (shaving hair and antiseptic treatment) a longitudinal 0.5-1.0 cm incision through rat skin was made and the surgical wound was kept open using holders. The luminescently labeled alginate implant, prepared according to Example 14, was implanted into the rat hip muscle through the incision and the wound was sutured.

Example 16

Detection of Environment-Insensitive Dye-Labeled Alginate Hydrogel and its Degradation Products in the Rat Myocardium Treatment of a solution of sodium alginate fluorescently labeled with the dye SeTau-405-NHS (SETA BioMedicals) with calcium gluconate solution obtained according to Example 12 does not lead to the formation of hydrogels neither in-vivo in biological tissues, nor in-vitro. The luminescently labeled sodium alginate solution introduced in the rat myocardium remains a non-viscous liquid, which can be detected by its luminescence. The luminescent image was recorded using fluorescent microscope LOMO "Lyumam K-1" with lens LOMO LK190 43×1.0 and camera "CAM-690C" 20. The image was taken at 20 minutes after the alginate introduction in the myocardium. The excitation was done with a Xenon Lamp (120 W) and a 390/10 bandpass filter. The luminescent image was obtained and recorded using a green 500 nm longpass filter. The obtained images allow detection and location the alginate in the myocardium.

Example 17

Use of the Viscosity-Insensitive Dye FITC for Monitoring of the Change in the Localization of the Alginate Hydrogel and its Degradation Products in the Rat Myocardium A FITC labeled alginate (Example 8) was implanted into the rat myocardium at a depth of 0.5-1 mm as described in Example 12. Along with the heart a luminescent standard of brightness, made of the same labeled implant, was placed. Images were taken at time intervals of 20 minutes, 1, 4 and 18 hours. The heart was illuminated at a 10 cm distance using a 470 nm LED (3 W) and 470/10 bandpass filter, and the luminescence was observed and recorded through the 430/55 bandpass filter green channel).

The luminescence images obtained in the green channel at different time periods demonstrate the possibility of monitoring hydrogels together with its degradation products.

Example 18

Alginate Images in Rat Hip

Figure 7:
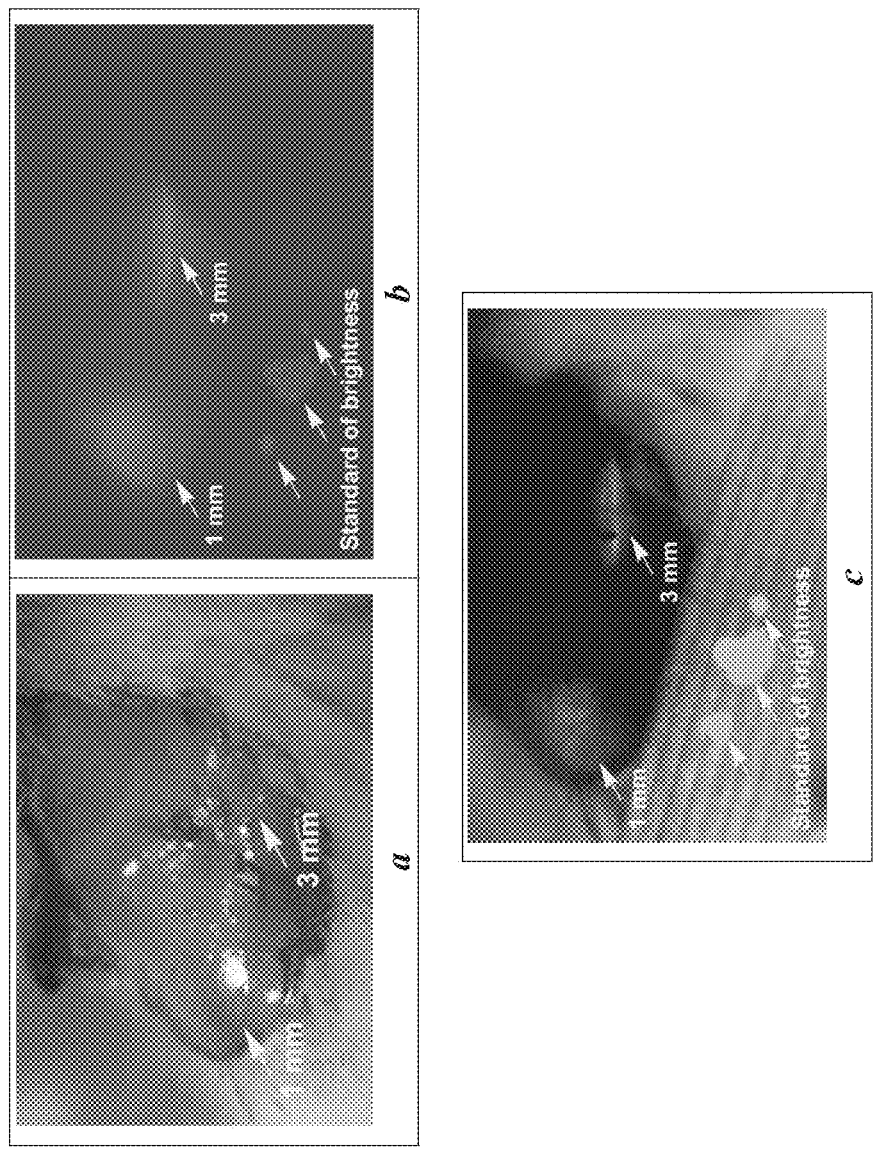
FIG. 7 Dense alginate implant fluorescently labeled with Dyes 9 and Seta-670 dye (1:1) injected in rat hip at a depth of 1 mm and 3 mm, in normal light (a) and in fluorescence mode: red channel, excitation 636 nm, 640/10 bandpass excitation filter, 670 nm longpass emission filter (b) and green channel, excitation 470 nm, 470/10 bandpass excitation filter, 546/20 bandpass emission filter (c).

The labeled alginate hydrogels obtained in Example 6 or Example 7 were injected into the rat hip as described in Example 11 and the images were taken at certain time periods in normal light and in the fluorescence regime in the green and red channels for 9-Seta-650-Alg or orange and red channels for 10-Seta-650-Alg (FIGS. 7 and 8).

Figure 9:
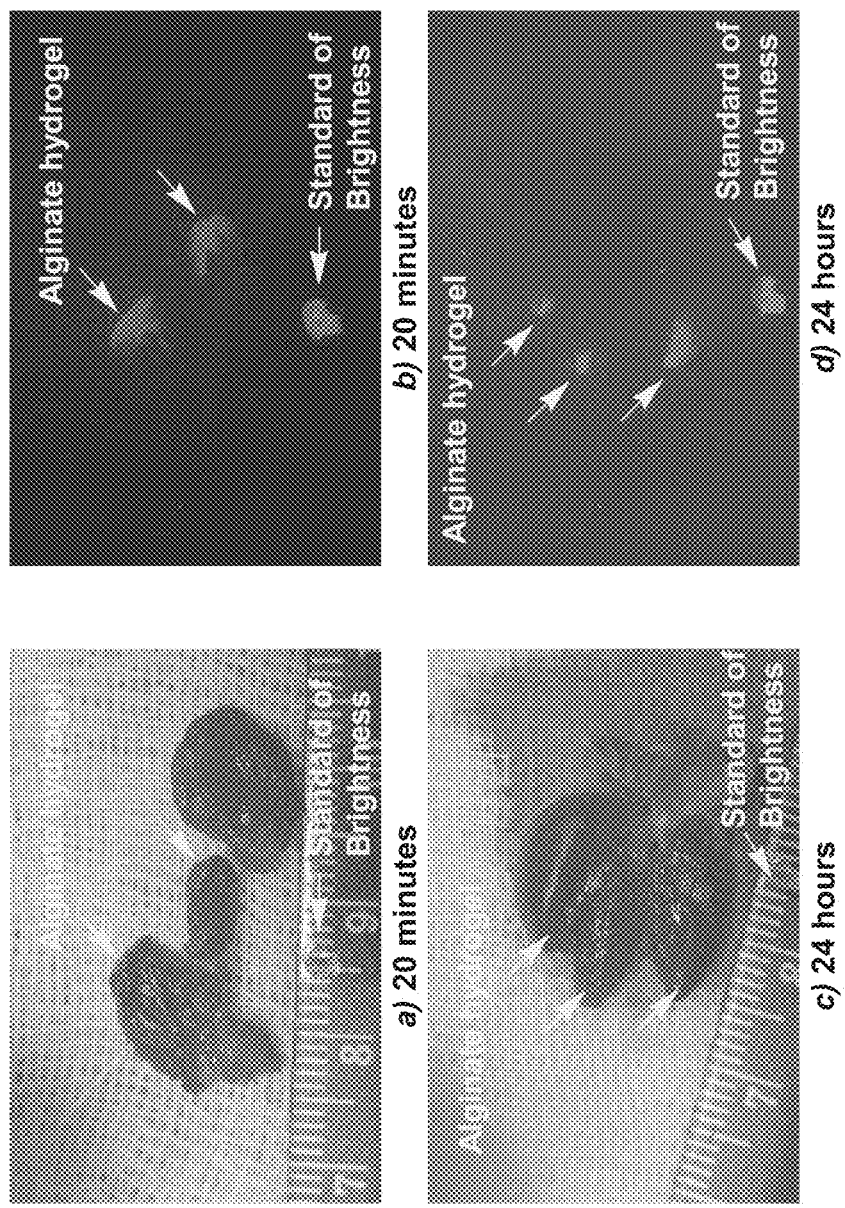
FIG. 9 Detection of the alginate implant and its degradation products in rat myocardium by environment-insensitive dye Seta-650: in normal light 20 minutes (a) and 24 hours (c) after injection, and in fluorescence mode: red channel, excitation 636 nm, 640/10 bandpass excitation filter, 670 longpass emission filter at 20 minutes (b) and 24 hours (d) after injection.

The fluorescence images of the hydrogel exhibit an increase of the green/orange and red fluorescence areas after 1 hour. The increase can be attributed to the diffusion (spreading) of the hydrogel and its movement closer to the surface. Within 1-3 days after the alginate hydrogel is implanted a decrease in the green/orange fluorescence area of Dye 9/Dye 10 was observed. After 3 days of the implantation the green/orange emission intensity of Dye 9/Dye 10 becomes undetectable, while the red fluorescence area of Seta-650 remained almost unchanged starting from the $2^{nd}$ day and to at least 12 weeks after implantation.
Alginate Images in Rat Myocardium The alginate hydrogel, obtained by the Example 6 or Example 7 was injected into the rat myocardium as described in the Example 12. The images were acquired at certain time periods at normal light and in the fluorescence regime in the green and red channels for 9-Seta-650-Alg or orange and red channels for 10-Seta-650-Alg (FIG. 9).

Figure 10:
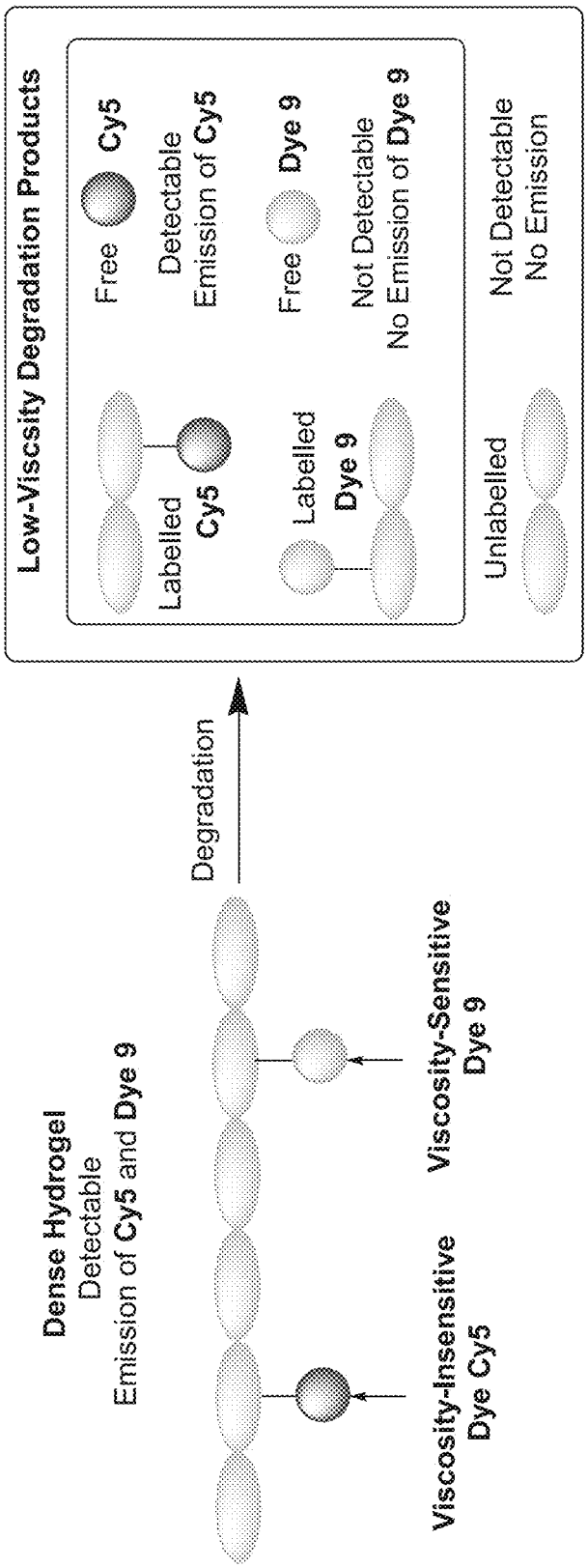
FIG. 10 A combination of the viscosity-sensitive Dye 9 and environment-insensitive dye Cy5 enables the detection of (1) the dense hydrogel labeled with 2 dyes (both dyes fluoresce); (2) hydrogel degradation products labeled with environment-insensitive dye; and (3) free environment-insensitive dyes eliminated from hydrogel during degradation. Viscosity-sensitive dyes fluoresce only in the dense hydrogel but are almost non-fluorescent in aqueous solution and when bound to non-viscous hydrogel degradation products.

The location of the gel implant in each heart was found visually by its fluorescence signal obtained in the red channel. Then the heart was cut at the place of the maximal concentration of the fluorescing implant and the images were taken for the green and red channels for 9-Seta-650-Alg and 9-Cy5-Alg or orange and red channels for 10-Seta-650-Alg and 10-Cy5-Alg (FIG. 10).

Example 19

Detection of the Diffusion of Hydrogel Carrier in the Rat Hip Using Three Dyes: Dye 9, Seta-555 and SeTau-647

An alginate hydrogel was prepared according to Example 6 by covalently attaching the viscosity-sensitive green dye 9 and the viscosity-insensitive orange and red dyes Seta-555 and SeTau-647 in a molar ratio of 1:1:1. It was then injected at a depth of 3 mm into the rat hip. A small piece (1-2 mm diameter) of the same fluorescently labeled dense alginate was spotted on the black ruler at a distance of 1-3 cm from the injected alginate and utilized as a brightness standard. Images of a biological sample containing the injected hydrogel were taken at 30 minutes, 18, 24, 48 and 72 hours after the injection. The fluorescent images obtained for the green, orange and red channels at certain time intervals after administration of hydrogel indicated that these areas changed over time: The green, orange and red fluorescence areas increase during 1 hour. The increase can be attributed to the diffusion (spreading) of the hydrogel and its movement closer to the surface. Within 1-3 days after the alginate hydrogel is implanted a decrease in the green fluorescence area of Dye 9 was observed. After 3 days of the implantation the green emission intensity of Dye 9 becomes undetectable, while the orange and red fluorescence areas of Seta-555 and SeTau-647 took longer to decrease (1-3 weeks). Importantly, the region of emission of dye Seta-555 (orange area) changed faster than the area of red dye SeTau-647. This is because of the higher molecular weight of the SeTau-647 dye as compared to the Seta-555 dye. This demonstrates the ability to monitor the diffusion rates of low molecular weight organic compounds, including pharmaceuticals in real-time at this time-scale.

Example 20

Figure 11:
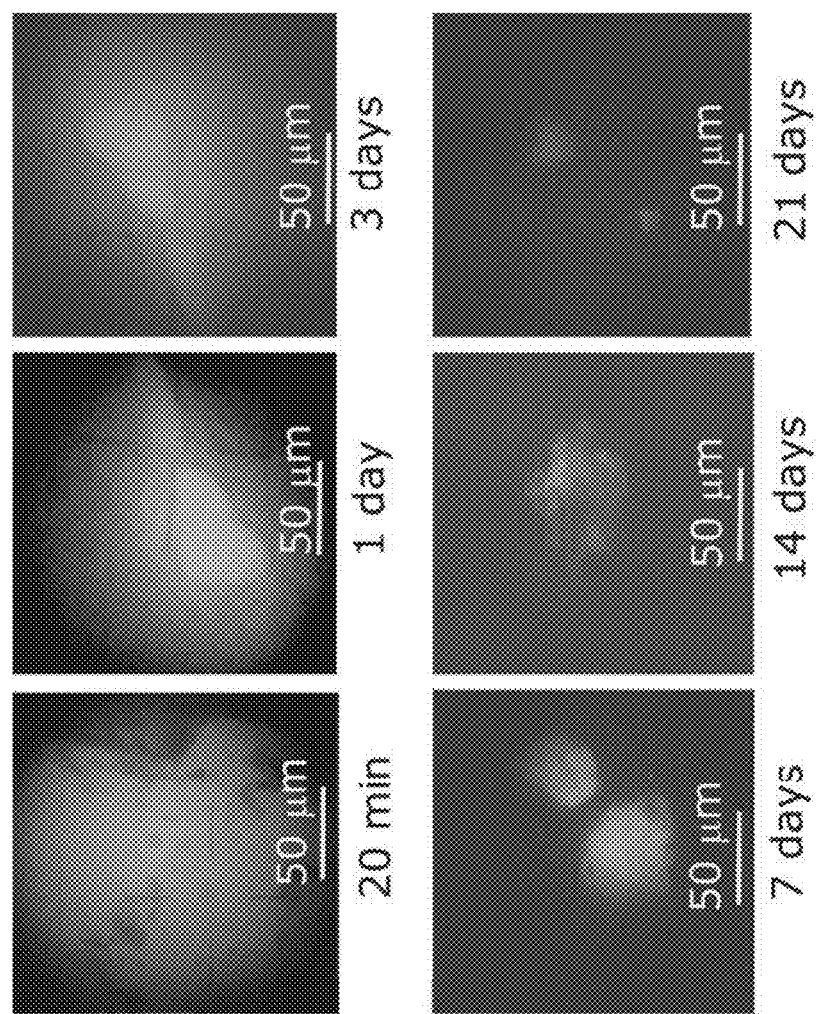
FIG. 11 Change in viscosity of alginate hydrogel implant stained with viscosity-sensitive Dye 9 as measured by fluorescence microscopy set up.

Use of the Viscosity-Sensitive Dye 9 for Monitoring the Localization of the Dense Alginate Hydrogel in the Rat Myocardium The alginate hydrogel fluorescently labeled with the Dye 9 (Example 4) was injected into the rat myocardium as described in the Example 12. The luminescent image was recorded using fluorescent microscope LOMO "Lyumam K-1" with lens LOMO LK190 43×1.0 and camera "CAM-690C" 20. The image was taken at 20 minutes, 1, 3, 7, 14, and 21 days after administration of the hydrogel in the myocardium. The excitation was done with a Xenon Lamp (120 W with) and a 448/20 nm bandpass filter. The luminescent image was observed and recorded using a green 500 nm longpass filter. The obtained images demonstrate the ability to detect the dense hydrogel including the possibility to trace it in the myocardium for at least 21 days (FIG. 11, 12).

DESCRIPTION OF APPLICATIONS

The compounds according to the present disclosure are in particular useful for viscosity measurement in biological samples in general or specifically the detection of hydrogel and/or hydrogel degradation products.

This is achieved using luminescent dyes that are sensitive to the viscosity of the environment, or simultaneously using at least two luminescent dyes with at least one being sensitive to the viscosity of the hydrogel, and the other being insensitive to viscosity, polarity and hydrophilicity of the environment. Moreover, if these dyes have different spectral characteristics, such as the different excitation and/or emission wavelengths and/or different luminescence lifetimes, the different characteristics allow one to differentiate between the localization of the dense hydrogel and the degraded hydrogels of low viscosity.

Dyes that are insensitive to viscosity, polarity and hydrophylicity are well known and are based on cyanines, xanthenes, coumarines, metal-ligand complexes, lanthanides, among others. Any of these dyes are suitable to be used as environment-insensitive dyes in our proposed method as long as they do not exhibit a change in their spectral properties due to changes in the viscosity, polarity and hydrophilicity of the environment.

Methods according to the present disclosure may be capable of the following:

1) Localization of the dense hydrogel (Example 18) (FIG. 12);
2) Localization of the dense hydrogel together with its degradation products (Example 18) (FIG. 10);
3) Localization of the hydrogel degradation products (Example 16 and 17); and
4) Determination of the rheological state of the hydrogel and differentiation between the localization of dense hydrogel having a high viscosity, and its degradation products with a lower viscosity (Example 18). Our novel method enables monitoring the rheological state and viscosity of hydrogel biostructural materials (FIG. 10) including surgical implants, and also to study transport and targeted delivery of drugs in real-time.

Hydrogels may include collagen, gelatin, alginate, chitosan, PEGylated, PEG-dextran, aminopolysacharid, carboxymetylcellulose, acrylic, and poly(vinylpirrolidone) hydrogel among others (Examples 11, 12, 13, and 14). Importantly, for the implementation of this method, the hydrogel may be covalently labeled with one or more fluorescent dyes. The luminescently labeled hydrogel can be obtained by linking the dye to a ready-made hydrogel, which is then placed into the biological tissue by implantation (Examples 11-12 and 15), or linking the dye to a hydrogel precursor (Examples 3-10), which is then thickened or polymerized. The thickening process can either be done outside the biological tissue (Example 14), followed by implantation (Example 15), or in-situ in biological tissues as described in Examples 11-13.

The proposed methods also require a careful selection of fluorescent dyes for each hydrogel in accordance with the desired characteristics and depending on the specific problem to be solved. Our studies have shown that the viscosity sensitive squaraine dyes 9 and 10 can be successfully used to monitor dense alginate hydrogel and study its viscosity changes over time (Examples 18 and 19). At the same time, we found that the fluorescent naphthalimide dye SeTau-405 inhibits gelation of alginates covalently labeled with this dye. On the other hand, this dye is suitable for identification of the localization of non-gelated alginate in biological tissues (Example 16). Cyanine dyes Seta 650 and Cy5 and fluorescein (FITC) can be used to monitor the dense hydrogel together with its degradation products or to study the hydrogel implants resorption (Examples 17 and 18). The squaraine-rotaxane dye SeTau-647 is suitable for long-term monitoring of a hydrogel and/or its degradation products of (Example 19).

The blue, green and yellow light, which corresponds to a wavelength less than about 600 nm, is known to be highly absorbed by biological tissues and therefore can be used only to obtain a luminescence signal from the surface of tissues at depths not exceeding more than 1 mm. To obtain fluorescence signals in tissue at longer distances (few millimeters to centimeters), longer-wavelength dyes that absorb and/or emit light in the red and near infrared spectral range from about 600 nm to 900 nm are useful (Examples 18 and 19).

For the simultaneous measurement of hydrogels with different rheological states (dense or degraded) it is proposed to use at least two luminescent dyes where at least one is sensitive to the viscosity of the hydrogel, and the other one is insensitive to the environment viscosity, polarity and hydrophilicity. This is demonstrated in the Examples 18 and 19 using the Dyes 9 and 10, which are sensitive to the viscosity of the hydrogel, and Dyes Cy5 or SeTau-647 dye, which are insensitive to the environment viscosity, polarity and hydrophilicity. These dyes have different excitation and emission maxima, allowing to distinguish their luminescence signal and thereby to differentiate the localization of the dense hydrogel and its degradation products. The ability to monitor the diffusion of low molecular weight organic compounds, including drugs, using three dyes (9, Seta-555 and SeTau-647) in real time is demonstrated in Example 19.

Using the well characterized p53-Mdm2 interaction as a model system, the mono-squaraines of the present disclosure could be used instead of julolidine molecular rotors in the p53 peptide reporter, JP1-R, which fluoresces conditionally only upon Mdm2 binding (W. L. Goh et al., *J. Am. Chem. Soc.*, 2014, 136 (17), pp 6159-6162). The julolidine reporter was used in a rapid, homogeneous assay to screen a fragment library for antagonists of the p53-Mdm2 interaction, and several inhibitors were identified. Subsequent validation of these hits using established secondary assays suggests increased sensitivity afforded by JP1-R. The luminescence of molecular rotors contingent upon target binding makes them a versatile tool for detecting specific biomolecular interactions.

Luminescence Methods

The disclosed reporter compounds may be detected using common intensity-based or lifetime based luminescence methods. The mono-squaraine dyes are known to have lifetimes in the range of hundreds of picoseconds (ps). Notably, the lifetime and quantum yields increase upon increasing the viscosity of the environment. The fluorescence lifetime can therefore be directly correlated to viscosity.

Changing the viscosity of the environment will have an effect on the lifetime and therefore also on the fluorescence polarization of the dye. Mono-squaraine dyes are therefore useful for the measurement of the environment viscosity by fluorescence polarization.

Compositions and Kits

The present disclosure also encompasses compositions, kits and integrated systems for practicing the various methods of the present disclosure.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The various disclosed elements of systems and steps of methods disclosed herein are not required of all systems, apparatuses, and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system, apparatus, or method. Accordingly, such inventive subject matter is not required to be associated with the specific systems, apparatuses, and methods that are expressly disclosed herein, and such inventive subject matter may find utility in systems, apparatuses, and/or methods that are not expressly disclosed herein.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A method of analyzing a sample, the method comprising:
   labeling a sample with a viscosity-sensitive luminescent dye to form a labeled sample, wherein the viscosity-sensitive luminescent dye is sensitive to a viscosity of a local environment of the viscosity-sensitive luminescent dye;
   exciting at least a portion of the sample with excitation energy to produce emission light from the viscosity-sensitive luminescent dye, wherein the excitation energy includes at least one of UV light, visible light, NIR light, and ultrasonic energy; and
   detecting the emission light from the viscosity-sensitive luminescent dye;
   wherein the viscosity-sensitive luminescent dye has the following structure:

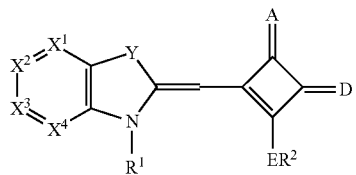

where A and D are selected from the group consisting of $=O$, $=S$, $=Se$, $=Te$, $=N-R^a$, and $=C(R^b)(R^c)$;
E is selected from the group consisting of $-O-$, $-S-$, $-Se-$, $-Te-$, $-(N-R^a)-$, and $-(C(R^b)(R^c))-$;
$R^2$ is selected from the group consisting of H, alkyl, and a positive counter-ion;

$R^a$ is selected from the group consisting of H, aliphatic, aromatic, alicyclic, aryl-alkyl, linked carriers, reactive substituents, reactive aliphatic substituents, $-COOH$, $-CN$, and $-OH$;

$R^b$ and $R^c$ are independently selected from the group consisting of H, aliphatic, aromatic, alicyclic, aryl-alkyl, -L-$S_c$, -L-$R^x$, -L-$R^\pm$, $-COOH$, $-CN$, $-OH$, $-SO_3H$, $-PO_3H_2$, $-O-PO_3H_2$, $-PO_3R_2^m$, $-O-PO_3R_2^m$, $-CONHR^m$, $-CONH_2$, $-COO-NHS$ and $-COO-R^m$; each aliphatic residue may incorporate up to 20 heteroatoms selected from N, O, and S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; or adjacent $R^b$ and $R^c$, taken in combination, form a cyclic or heterocyclic ring structure that is optionally substituted by -L-$S_c$, -L-$R^x$ or -L-$R^\pm$;

$R^m$ is selected from the group consisting of aliphatic groups, $-(CH_2)_y-S_c$, $-(CH_2)_y-R^x$, $-(CH_2)_y-R^\pm$, $-(CH_2)_y-O-(CH_2)_y-S_c$, $-(CH_2)_y-O-(CH_2)_y-R^x$, $-(CH_2)_y-O-(CH_2)_y-R^\pm$, and aromatic substituents, where each y is independently 1 to 20;

L is a covalent linkage that is linear or branched, cyclic or heterocyclic, saturated or unsaturated, having 1-60 nonhydrogen atoms from the group consisting of C, N, P, O and S, in such a way that the linkage contains any combination of ether, thioether, amine, ester, amide bonds; single, double, triple or aromatic carbon-carbon bonds; carbon-sulfur bonds, carbon-nitrogen bonds, phosphorus-sulfur bonds, nitrogen-nitrogen bonds, nitrogen-oxygen bonds, nitrogen-platinum bonds, or aromatic or heteroaromatic bonds;

$R^x$ is a reactive group;

$S_c$ is a conjugated substance;

$R^\pm$ is an ionic group;

Y is independently selected from the group consisting of O, S, N—$R^d$, $CR^e=CR^f$ and $C(R^i)(R^j)$, wherein $R^d$ is selected from the group consisting of H, aliphatic groups, alicyclic groups, aromatic groups, -L-$S_c$, -L-$R^x$, -L-$R^\pm$, and $-CH_2-CONH-SO_2$-Me;

$R^e$, $R^f$, $R^i$, and $R^j$ are independently selected from the group consisting of H, aliphatic groups, alicyclic groups, aromatic groups, -L-$S_c$, -L-$R^x$, -L-$R^\pm$, $-R^x$, $-R^\pm$, $-CH_2-CONH-SO_2$-Me, $-COOH$, $-CN$, $-OH$, $-SO_3H$, $-PO_3H_2$, $-O-PO_3H_2$, $-PO_3R_2^m$, $-O-PO_3R_2^m$, $-CONHR^m$, $-CONH_2$, $-COO-NHS$ and $-COO-R^m$; each aliphatic residue may incorporate up to 20 heteroatoms selected from N, O, and S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; or $R^i$ and $R^j$, taken in combination, form a ring-system that is optionally further substituted by one or more reactive or ionic substituents;

$R^1$ is selected from the group consisting of H, aliphatic groups, alicyclic groups, alkylaryl groups, aromatic groups, -L-$S_c$, -L-$R^x$, -L-$R^\pm$, and $-CH_2-CONH-SO_2$-Me; each aliphatic residue may incorporate up to 20 heteroatoms selected from N, O, S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

each of $X^1$, $X^2$, $X^a$, and $X^4$ are independently selected from the group consisting of N, $NR^K$, O, S, and C—$R^T$, where $R^K$ is hydrogen, alkyl, arylalkyl and aryl groups, -L-$S_c$, -L-$R^x$, -L-$R^\pm$, or —$CH_2$—CONH—$SO_2$-Me, where each aliphatic residue may incorporate up to 20 heteroatoms selected from N, O, S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; $R^T$ is hydrogen, -L-$S_c$, -L-$R^x$, -L-$R^\pm$, —$R^x$, —$R^\pm$, —$CH_2$—CONH—$SO_2$-Me, amino, alkylamino, dialkylamino, trialkylammonium, sulfo, trifluoromethyl, alkoxy, halogen, carboxy, hydroxy, phosphate, sulfate, an aliphatic group, an alicyclic group, or aromatic group; each aliphatic residue may incorporate up to 20 heteroatoms selected from N, O, S, and may be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; or adjacent $R^K$ substituents, $R^T$ substituents, or $R^K$ and $R^T$ substituents, taken in combination, form a fused aromatic or heterocyclic ring that is optionally substituted by H, alkyl, aryl, cycloalkyl L-$S_c$, L-$R^x$, L-$R^\pm$, —$R^x$ or —$R^\pm$; and each H may be independently substituted by a fluorine.

2. The method of claim 1, wherein the viscosity-sensitive luminescent dye at least one of absorbs and emits light within a range of 400-950 nm.

3. The method of claim 1, wherein the detecting includes detecting by at least one of fluorescence imaging and fluorescence lifetime imaging (FLIM).

4. The method of claim 1, where the viscosity-sensitive luminescent dye has the following structure:

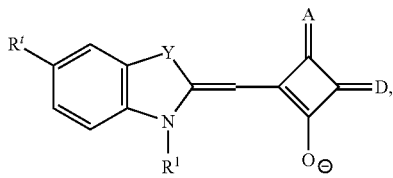

wherein where A and D are selected from the group consisting of =O, =S, =Se, =Te, =N—$R^a$, and =C($R^b$)($R^c$).

5. The method of claim 1, wherein labeling the sample includes covalently labeling a hydrogel component with the viscosity-sensitive luminescent dye to form a labeled hydrogel component and includes incorporating the labeled hydrogel component into the sample to form a labeled hydrogel within the sample.

6. The method of claim 5, where the labeled hydrogel is an alginate hydrogel.

7. The method of claim 5, wherein covalently labeling the hydrogel component includes covalently labeling a hydrogel including the hydrogel component.

8. The method of claim 5, wherein incorporating the labeled hydrogel component includes forming the labeled hydrogel in situ in the sample by injecting the labeled hydrogel component into the sample.

9. The method of claim 8, wherein forming the labeled hydrogel includes injecting into the sample an aqueous solution of at least one of alkali metal alginate, alkali earth metal ions, and transition metal ions.

10. The method of claim 5, wherein the sample is a biological sample, wherein the method further comprises labeling the biological sample with an environment-insensitive luminescent dye, wherein luminescence emission from the environment-insensitive luminescent dye is substantially unaffected by a viscosity, a polarity, and a hydrophilicity of a local environment of the environment-insensitive luminescent dye, wherein the exciting includes exciting the biological sample with excitation energy to produce emission light from environment-insensitive luminescent dye, and wherein the detecting includes detecting the emission light from the environment-insensitive luminescent dye.

11. The method of claim 10, wherein the labeling the biological sample with the environment-insensitive luminescent dye includes covalently labeling the hydrogel component with the environment-insensitive luminescent dye.

12. The method of claim 10, wherein the viscosity-sensitive luminescent dye has a different luminescent property than a corresponding property of the environment-insensitive luminescent dye, wherein the luminescent property is one of excitation spectrum, emission spectrum, and luminescence lifetime.

13. The method of claim 10, wherein the environment-insensitive luminescent dye at least one of absorbs and emits light within a range of 400-950 nm.

14. The method of claim 10, wherein the environment-insensitive luminescent dye is at least one of a photosensitizer, a photosonic dye, and a photoacoustic dye, and wherein the environment-insensitive dye is adapted for at least one of photodynamic therapy, photodynamic antimicrobial chemotherapy, and antimicrobial coating.

* * * * *

UNITED STATES PATENT AND TRADEMARK OFFICE
CERTIFICATE OF CORRECTION

PATENT NO. : 9,841,428 B2  
APPLICATION NO. : 14/866067  
DATED : December 12, 2017  
INVENTOR(S) : Tetiana Vitaliivna Shkand et al.

Page 1 of 1

It is certified that error appears in the above-identified patent and that said Letters Patent is hereby corrected as shown below:

In the Claims

Column 32, Line 66, Claim 1, after "each of $X^1$, $X^2$," please delete "$X^a$" and insert -- $X^3$ --.

Signed and Sealed this  
Thirtieth Day of January, 2018

Joseph Matal  
*Performing the Functions and Duties of the*  
*Under Secretary of Commerce for Intellectual Property and*  
*Director of the United States Patent and Trademark Office*